(12) United States Patent
Hirata et al.

(10) Patent No.: US 10,676,561 B2
(45) Date of Patent: Jun. 9, 2020

(54) (METH)ACRYLAMIDE BASED URETHANE OLIGOMER AND ACTIVE ENERGY RAY CURABLE RESIN COMPOSITION CONTAINING SAME

(71) Applicant: KJ CHEMICALS CORPORATION, Tokyo (JP)

(72) Inventors: Meiri Hirata, Tokyo (JP); Miki Takenouchi, Kumamoto (JP); Yusuke Adachi, Kumamoto (JP); Kouji Teramoto, Kumamoto (JP)

(73) Assignee: KJ CHEMICALS CORPORATION, Tokyo (JP)

( * ) Notice: Subject to any disclaimer, the term of this patent is extended or adjusted under 35 U.S.C. 154(b) by 135 days.

(21) Appl. No.: 15/754,854

(22) PCT Filed: Sep. 14, 2016

(86) PCT No.: PCT/JP2016/077053
§ 371 (c)(1),
(2) Date: Feb. 23, 2018

(87) PCT Pub. No.: WO2017/047615
PCT Pub. Date: Mar. 23, 2017

(65) Prior Publication Data
US 2018/0244831 A1    Aug. 30, 2018

(30) Foreign Application Priority Data

Sep. 16, 2015  (JP) ................................. 2015-183475
Sep. 2, 2016   (JP) ................................. 2016-172327

(51) Int. Cl.
| | | |
|---|---|---|
| C08G 18/00 | (2006.01) | |
| C08G 18/67 | (2006.01) | |
| C09D 4/00 | (2006.01) | |
| C09D 11/30 | (2014.01) | |
| C09K 3/10 | (2006.01) | |
| C08F 290/06 | (2006.01) | |
| C08G 18/48 | (2006.01) | |
| C09D 175/16 | (2006.01) | |

(Continued)

(52) U.S. Cl.
CPC ............ *C08G 18/6705* (2013.01); *A61K 8/87* (2013.01); *A61Q 3/02* (2013.01); *B33Y 10/00* (2014.12); *C08F 290/06* (2013.01); *C08G 18/10* (2013.01); *C08G 18/12* (2013.01); *C08G 18/242* (2013.01); *C08G 18/246* (2013.01); *C08G 18/4009* (2013.01); *C08G 18/4018* (2013.01); *C08G 18/4063* (2013.01); *C08G 18/42* (2013.01); *C08G 18/4202* (2013.01); *C08G 18/44* (2013.01); *C08G 18/4808* (2013.01); *C08G 18/4825* (2013.01); *C08G 18/4833* (2013.01); *C08G 18/4854* (2013.01); *C08G 18/61* (2013.01); *C08G 18/6216* (2013.01); *C08G 18/73* (2013.01); *C08G 18/755* (2013.01); *C08G 18/758* (2013.01); *C08G 18/7837* (2013.01); *C08G 18/792* (2013.01); *C09D 4/00* (2013.01); *C09D 11/101* (2013.01); *C09D 11/30* (2013.01); *C09D 175/16* (2013.01); *C09J 4/00* (2013.01); *C09J 175/16* (2013.01); *C09K 3/10* (2013.01); *A61K 2800/94* (2013.01); *A61K 2800/95* (2013.01); *C08G 2105/02* (2013.01); *C08G 2190/00* (2013.01)

(58) Field of Classification Search
CPC ...................................................... C08G 18/00
See application file for complete search history.

(56) References Cited

U.S. PATENT DOCUMENTS

| 9,738,748 B2 * | 8/2017 | Takenouchi ........... C08G 18/44 |
|---|---|---|
| 2004/0013976 A1 | 1/2004 | Fujimoto et al. |

(Continued)

FOREIGN PATENT DOCUMENTS

| JP | 61-21120 A | 1/1986 |
|---|---|---|
| JP | 06-145276 A | 5/1994 |

(Continued)

OTHER PUBLICATIONS

International Search Report from Patent Application No. PCT/JP2016/077053, dated Dec. 6, 2016.

(Continued)

*Primary Examiner* — Rip A Lee
(74) *Attorney, Agent, or Firm* — Greenblum & Bernstein, P.L.C.

(57) ABSTRACT

An object is to provide a (meth)acrylamide based urethane oligomer which has excellent compatibility with organic solvents and general purpose acrylic monomers and oligomers, a high curing property with an active energy ray, and a low curing shrinkage property, and to provide an active energy ray curable resin composition containing the same which has an excellent adhesion property, moisture resistance, surface curing property, and also a low curing shrinkage property, and a molded article of the same. By using a (meth)acrylamide based urethane oligomer characterized by having a (meth)acrylamide group at the end or in side chain thereof and a cure shrinkage rate of 5% or less, it is possible to prepare a urethane oligomer having high curing property and excellent compatibility with organic solvents and general purpose acrylic monomers and oligomers, and an active energy ray curable resin composition containing the same and having excellent adhesion property can be prepared.

13 Claims, No Drawings

(51) Int. Cl.

| | | |
|---|---|---|
| *C08G 18/40* | (2006.01) | |
| *C08G 18/42* | (2006.01) | |
| *C08G 18/75* | (2006.01) | |
| *C08G 18/24* | (2006.01) | |
| *C08G 18/78* | (2006.01) | |
| *B33Y 10/00* | (2015.01) | |
| *C09J 175/16* | (2006.01) | |
| *C08G 18/79* | (2006.01) | |
| *C08G 18/62* | (2006.01) | |
| *C08G 18/44* | (2006.01) | |
| *C08G 18/61* | (2006.01) | |
| *C08G 18/12* | (2006.01) | |
| *C08G 18/73* | (2006.01) | |
| *A61K 8/87* | (2006.01) | |
| *A61Q 3/02* | (2006.01) | |
| *C08G 18/10* | (2006.01) | |
| *C09D 11/101* | (2014.01) | |
| *C09J 4/00* | (2006.01) | |

(56) References Cited

U.S. PATENT DOCUMENTS

| | | |
|---|---|---|
| 2008/0102394 A1 | 5/2008 | Pang et al. |
| 2017/0009001 A1 | 1/2017 | Takenouchi et al. |

FOREIGN PATENT DOCUMENTS

| | | | | |
|---|---|---|---|---|
| JP | 2001-125257 A | | 5/2001 | |
| JP | 2002-37849 A | * | 2/2002 | ............... C08F 2/46 |
| JP | 2008-45032 A | * | 2/2008 | ............ C08F 290/06 |
| JP | 2009-244460 A | * | 10/2009 | ............ G03G 15/00 |
| JP | 2010-128417 A | | 6/2010 | |
| JP | 2010-267703 A | | 11/2010 | |
| JP | 2011-218616 A | | 11/2011 | |
| JP | 2012-082288 A | | 4/2012 | |
| JP | 2013-227519 A | | 11/2013 | |
| JP | 2016-113518 A | * | 6/2016 | ............ C08F 290/06 |
| WO | 2013/088889 A1 | | 6/2013 | |
| WO | 2015/141537 A | | 9/2015 | |
| WO | WO 2015/141537 A1 | * | 9/2015 | ............ C08F 299/06 |

OTHER PUBLICATIONS

International Preliminary Report on Patentability from Patent Application No. PCT/JP2016/077053, dated Mar. 20, 2018.
Notification of Reasons for Refusal for Patent Application No. 2017-518368 dated Jul. 4, 2017.
Notification of Reasons for Refusal for Patent Application No. 2017-518368 dated Sep. 13, 2017.
Notification of Reasons for Refusal for Patent Application No. 2017-518367 dated Jul. 4, 2017.
U.S. Appl. No. 15/754,160, filed Feb. 21, 2018.
Extended European Search Report from Application No. EP 16846486.5 dated Apr. 15, 2019.
Communication pursuant to Rules 70(2) and 70a(2) EPC from Application No. EP 16846486.5 dated May 3, 2019.

* cited by examiner

(METH)ACRYLAMIDE BASED URETHANE OLIGOMER AND ACTIVE ENERGY RAY CURABLE RESIN COMPOSITION CONTAINING SAME

TECHNICAL FIELD

The present invention relates to a (meth)acrylamide based urethane oligomer which has excellent compatibility with organic solvents and general purpose acrylic monomers and oligomers, a high curing property with an active energy ray, and a cure shrinkage rate of 5% or less. The present invention further relates to an active energy ray curable resin composition containing the (meth)acrylamide based urethane oligomer, which has an excellent adhesion property, moisture resistance, and surface curing property, and also a low curing shrinkage property and high transparency. The present invention still further relates to a molded article of the active energy ray curable resin composition.

BACKGROUND ART

Most of the polymerizable urethane oligomers are urethane acrylate. By having various skeleton structures with good balance, it can easily provide many performances like plasticity, bending property, flexibility, toughness, solvent resistance, and abrasion resistance. Due to such reasons, the polymerizable urethane oligomers are widely used in many fields including cohesives, coatings, and inks. As for the urethane acrylate, by reacting first polyol with polyisocyanate in general, polyurethane having a hydroxyl group or an isocyanate group at both ends is obtained. After that, according to a further reaction between the polyurethane and acrylate containing a hydroxyl group or acrylate containing an isocyanate group, urethane acrylate is synthesized (Patent Literatures 1 to 3). Also suggested is a synthetic method in which acrylate containing a hydroxyl group is reacted with polyisocyanate and the reaction product is linked to polyol terminal (Patent Literature 4).

Urethane acrylate has a radical polymerizable acrylate group. Accordingly, similar to monofunctional acrylate, polyfunctional acrylate, and epoxy acrylate, it is widely used as a constitutional component of an active energy ray curable resin composition. Meanwhile, in accordance with an increased blending amount of urethane acrylate, the curing property of an entire composition decreases. As such, there is a problem that, when it is applied as a resin composition on a substrate and cured by irradiation of an active energy ray like ultraviolet ray, stickiness remains on a surface of a coating film, and thus it is difficult to have a tack free state. Furthermore, when an elastic layer with thickness is formed as a sealing material between a solar battery module and a frame, or a sealing material for semiconductors, liquid crystals, and LED, non-cured components are present in a large amount inside the layer. As such, sufficiently satisfying performances cannot be obtained. There is also a contamination problem which is caused by bleed out of non-cured components over time. As such, to solve the sticky residuals on a surface and non-curing inside a thick layer, combined use with monofunctional or polyfunctional acryl monomer or photosensitizer is reported. For example, in Patent Literature 1, a photocurable resin composition which is obtained by blending urethane acrylate with polybutadiene skeleton with 20 to 80% of monofunctional acrylate and 2% of a sensitizer is suggested. However, in most cases, solubility of the urethane acrylate with polybutadiene skeleton in an acrylate monomer is insufficient due to the influence of a polybutadiene structure having high hydrophobicity. Meanwhile, there is a problem that flexibility specific to the polybutadiene skeleton is deteriorated in accordance with use of the polyfunctional acrylate. There is also a problem that, as an acryl monomer is blended, it becomes difficult to maintain the cure shrinkage rate at a low level after irradiation of ultraviolet (UV) ray.

Furthermore, to improve overall the active energy ray curing property of a urethane acrylate resin, in particular, the hardness and surface stickiness of a cured product, an oligomer as an adduct of urethane acrylamide is suggested (Patent Literatures 5 to 8). By modifying the polymerizable group from an acrylate group to an acrylamide group, the ultraviolet ray curing property is enhanced, and stickiness on a surface of a cured film and hardness of a cured product are improved. However, no mention is made at all regarding the solubility for general purpose organic solvents and acrylic monomers, and transparency, scratch resistance, abrasion resistance, and curing shrinkage resistance of an obtained cured film.

CITATION LIST

Patent Literature

PATENT LITERATURE 1: JP 61-21120 A
PATENT LITERATURE 2: JP 2010-267703 A
PATENT LITERATURE 3: JP 6-145276 A
PATENT LITERATURE 4: WO 2013/088889
PATENT LITERATURE 5: JP 2002-37849 A
PATENT LITERATURE 6: JP 2009-244460 A
PATENT LITERATURE 7: JP 2011-218616 A
PATENT LITERATURE 8: JP 2012-082288 A

SUMMARY OF THE INVENTION

Problems to be Solved by the Invention

The present invention relates to a (meth)acrylamide based urethane oligomer which has excellent compatibility with organic solvents and general purpose acrylic monomers and oligomers, a high curing property with an active energy ray, and a low cure shrinkage property. The present invention further relates to an active energy ray curable resin composition containing the (meth)acrylamide based urethane oligomer, which has an excellent adhesion property, moisture resistance, and surface curing property, and also a low curing shrinkage property and high transparency. The present invention also provides a molded article of the active energy ray curable resin composition.

Solution to the Problems

The inventors of the present invention repeated intensive studies to solve the problems described above. As a result, it was found that the object can be achieved by using a (meth)acrylamide based urethane oligomer which has one or two or more kinds of a skeleton selected from an ether skeleton, an ester skeleton, a silicone skeleton, and an acryl skeleton in the molecule, at least one (meth)acrylamide group, and an active energy ray cure shrinkage rate of 5% or less. The present invention is achieved accordingly.

Effects of the Invention

According to the present invention, a (meth)acrylamide based urethane oligomer which is obtained by an addition reaction of polyol (A) which has at least one hydroxyl groups in one molecule and one or two or more skeletons selected from an ether skeleton, ester skeleton, silicone skeleton, and acryl skeleton, polyisocyanate (B) having at least two isocyanate groups in one molecule, and (meth) acrylamide (C) having a hydroxyl group is provided. The urethane oligomer can provide a (meth)acrylamide based urethane oligomer which does not contain any isocyanate group at the end, exhibits a shrinkage rate of 5.0% or less before and after active energy curing, and has excellent compatibility with organic solvents and general purpose acrylic monomers and oligomers and a high curing property with an active energy ray. Furthermore, by using the (meth) acrylamide based urethane oligomer of the present invention, an active energy ray curable resin composition having an excellent adhesion property, moisture resistance, and surface curing property, and also a low shrinkage property and high transparency can be provided. Furthermore, according to the present invention, a molded article thereof can be also provided.

DETAIL DESCRIPTION OF THE EMBODIMENTS

Hereinbelow, the present invention is explained in detail.

Characteristics of the (meth)acrylamide based urethane oligomer of the present invention lie in that it has one or two or more skeletons selected from an ether skeleton, ester skeleton, silicone skeleton, and acryl skeleton, has a (meth) acrylamide group at the end or in the side chain, and exhibits a cure shrinkage rate of 5.0% or less before and after active energy curing.

The (meth)acrylamide based urethane oligomer of the present invention (it may be also abbreviated as "urethane oligomer") is a compound which is obtained by an addition reaction of polyol (A) which has at least one hydroxyl groups in one molecule and one or two or more skeletons selected from an ether skeleton, ester skeleton, silicone skeleton, and acryl skeleton, polyisocyanate (B) having at least two isocyanate groups in one molecule, and (meth) acrylamide (C) having a hydroxyl group. This compound does not contain any isocyanate group at the end. Content of components having molecular weight of less than 1000 in the (meth)acrylamide based urethane oligomer of the present invention (excluding (meth)acrylamide having a hydroxyl group) is 5% by weight or less, preferably 3% by weight or less, and more preferably 1% by weight or less. Most of the low molecular weight components having molecular weight of less than 1000 are a urethane adduct compound which is obtained by an addition reaction between the polyisocyanate (B) and the (meth)acrylamide (C) having a hydroxyl group. It is assumed by the inventors of the present invention that the presence of this urethane adduct is a cause of having lower solubility of the urethane oligomer, an occurrence of cloudiness, surface sticking residuals caused by moisture absorption after active energy ray curing, and a decrease in the curing shrinkage resistance.

The method for synthesizing the (meth)acrylamide based urethane oligomer of the present invention is not particularly limited, and the urethane oligomer can be synthesized by a known technique for urethanization reaction. Namely, the urethane oligomer of the present invention can be synthesized from a reaction among monofunctional or polyfunctional alcohol (polyol) (A), polyisocyanate (B), and (meth) acrylamide monomer (C) having a hydroxyl group. Furthermore, from the viewpoint of further lowering the content of a component having molecular weight of less than 1000 (hereinbelow, also referred to as a low molecular weight component), as a preferred method, polyol and an isocyanate compound are reacted first with each other to synthesize a compound having at least one isocyanate group in the molecule. After that, according to a further reaction with a (meth)acrylamide monomer having a hydroxyl group, the target (meth)acrylamide based urethane oligomer is obtained.

Polyether polyol has a polyether main chain skeleton in the molecule and also one or more hydroxyl groups at the end of the main chain or in the side chain. Furthermore, from the viewpoint of having easy handlability, polyether polyol is preferably liquid at atmospheric temperature and atmospheric pressure. Examples of a commercially available product of the polyether polyol include Adeka Polyether P, BPX, G, T, EDP, AM, BM, CM, PR, and GR series (manufactured by ADEKA Corporation), diethylene glycol, dipropylene glycol, dibutylene glycol, PTMG series (manufactured by Mitsubishi Chemical Corporation), SANNIX PP, and GP, GOP series, for example, SANNIX PP-1000, GP-250, and GOP-600 (manufactured by Sanyo Kasei Kogyo K.K.), PEG series, UNIOX G series, UNIOL D, TG, and PB, UNILUBE DGP series, POLYCERIN DC, and DCB series (manufactured by NOF Corporation). Those polyether polyols may be used either singly or in combination of two or more kinds thereof.

Polyester polyol has a polyester main chain skeleton in the molecule and also one or more hydroxyl groups at the end of the main chain or in the side chain. Furthermore, from the viewpoint of having easy handlability, polyether polyol is preferably liquid at atmospheric temperature and atmospheric pressure. Examples of a commercially available product thereof include Adeka NEWACE series (manufactured by Adeka Corporation), Kuraray Polyol P, F, N, PMNA series (manufactured by Kuraray Co., Ltd.), PRIPLASTA series (manufactured by Croda), PRAXEL series (manufactured by Daicel Corporation), and TESLAC 2456 (manufactured by Hitachi Chemical Co., Ltd.). One kind of those polyester polyols may be used either singly or in combination of two or more kinds thereof.

Silicone polyol has a silicone main chain skeleton in the molecule and also one or more hydroxyl groups at the end of the main chain or in the side chain. Examples of a commercially available product thereof include KF-6000, X-21-5841 (manufactured by Shin Etsu Chemical Co., Ltd.), BY 16-201 manufactured by Toray Dow Corning), XF42-B0970 (manufactured by Momentive Performance Materials), and SILAPLANE series, for example, SILAPLANE FM-0411 (manufactured by JNC Corporation). One kind of those silicone polyols may be used either singly or in combination of two or more kinds thereof.

Acryl polyol is a polymer which is obtained by polymerizing one or more kinds of an acrylic monomer. This polymer has one or more hydroxyl groups at the end or in the side chain of the molecule. Examples thereof include a homopolymer obtained by using an acrylic monomer having a hydroxyl group such as hydroxyacryl (meth)acrylate or hydroxyacryl (meth)acrylamide and a copolymer with a monomer having other unsaturated group. Examples of a commercially available product thereof include UMM-1001 and UT-1001 (manufactured by Soken Chemical & Engineering Co., Ltd.).

As for the (meth)acrylamide based urethane oligomer, one or two or more polyols selected from the aforementioned polyether polyol, polyester polyol, silicone polyol, and acryl polyol can be used. In particular, (meth)acrylamide based urethane oligomer which contains two or more kinds of ester skeleton as an essential component and is obtained from diol having ester, ether, silicone, or acryl skeleton has an excellent adhesion property for copper. Among them, ester polyol is contained preferably at 30% by weight or more, and more preferably at 50% by weight or more.

Examples of the polyisocyanate (B) having two or more isocyanate groups in one molecule include aliphatic isocyanates such as trimethylene diisocyanate, hexamethylene diisocyanate, 1,2-butylene diisocyanate, or 2,4,4-trimethylhexamethylene diisocyanate, aromatic isocyanates such as 1,4-phenylene diisocyanate, 2,4-tolylene diisocyanate, 4,4'-diphenylmethane diisocyanate, and xylylene diisocyanate, alicyclic isocyanates such as cyclohexylene diisocyanate, isophorone diisocyanate, 4,4'-dicyclohexylmethane diisocyanate, 2,5-norbornane diisocyanate, or 2,6-norbornane diisocyanate, and alophanate group-containing isocyanates such as "DESMODUL XP2565" (manufactured by Sumika Bayer Urethane Co., Ltd.) or a multimer such as an adduct type, an isocyanurate type, or a burette type thereof, for example, Coronate L, HL, HX (manufactured by Nippon Polyurethane Industry Co., Ltd.), and DURANATE 24A-100 (manufactured by Asahi Kasei Corporation). One kind of those isocyanate monomers may be used either singly or in combination of two or more kinds thereof.

The (meth)acrylamide (C) having a hydroxyl group indicates methacrylamide containing hydroxyl group or acrylamide containing hydroxyl group. One kind of those acrylamides may be used either singly or in combination of two or more kinds thereof. Furthermore, use of the acrylamide having a hydroxyl group is particularly preferable as the curing property can be significantly enhanced.

Examples of the (meth)acrylamide having a hydroxyl group include N-hydroxymethyl (meth)acrylamide, N-hydroxyethyl (meth)acrylamide, N-hydroxypropyl (meth)acrylamide, N-hydroxyisopropyl (meth)acrylamide, N-methyl hydroxymethyl (meth)acrylamide, N-methyl hydroxyethyl (meth)acrylamide, N-methyl hydroxypropyl (meth)acrylamide, N-methylhydroxyisopropyl (meth)acrylamide, N-ethyl hydroxymethyl (meth)acrylamide, N-ethyl hydroxyethyl (meth)acrylamide, N-ethyl hydroxypropyl (meth)acrylamide, N-ethylhydroxyisopropyl (meth)acrylamide, N-propyl hydroxymethyl (meth)acrylamide, N-propyl hydroxyethyl (meth)acrylamide, N-propyl hydroxypropyl (meth)acrylamide, N-propylhydroxyisopropyl (meth) acrylamide, N-isopropyl hydroxyethyl (meth)acrylamide, N-isopropyl hydroxypropyl (meth)acrylamide, N-isopropylhydroxyisopropyl (meth)acrylamide, N,N-dihydroxymethyl (meth)acrylamide, N,N-dihydroxyethyl (meth)acrylamide, N,N-dihydroxy propyl (meth)acrylamide, and N,N-dihydroxy isopropyl (meth)acrylamide. In particular, N-hydroxyethyl (meth)acrylamide is preferred in that, as it has high refractive index (1.502), it can provide excellent transparency, has high safety and easy handlability due to low skin irritation (PII=0), and is easily obtainable as an industrial product with high purity. One kind of those (meth)acrylamides having a hydroxyl group may be used either singly or in combination of two or more kinds thereof.

The urethanization reaction can be carried out by a known method. In addition, the reaction can be performed in the absence of a solvent. However, as necessary, the reaction can be performed in an organic solvent or in a reactive diluent. Examples of the solvent which can be used include acetone, methyl ethyl ketone, methyl isobutyl ketone, cyclohexanone, dimethyl formamide, dimethyl acetamide, dimethyl sulfoxide, ethyl acetate, butyl acetate, tetrahydrofuran, hexane, cyclohexane, benzene, toluene, xylene and aliphatic hydrocarbon based solvents (petroleum ether), and the urethanization reaction can be performed in the presence of the above solvent. The reactive diluent which can be used is not particularly limited as long as it does not react with isocyanate, and examples thereof include methyl (meth)acrylate, ethyl (meth)acrylate, butyl (meth)acrylate, 2-ethylhexyl (meth)acrylate, cyclohexyl (meth)acrylate, 1,6-hexane diacrylate, tetraethylene glycol diacrylate, dipentaerythritol hexaacrylate, trimethylol propane triacrylate, isobornyl (meth)acrylate, dimethyl (meth)acrylamide, and di(meth)ethyl acrylamide, N-(meth)acryloyl morpholine. The use amount of an organic solvent or a reactive diluent is 0 to 400% by weight, and suitably 0 to 200% by weight relative to the isocyanate compound.

Furthermore, for the urethanization reaction, a catalyst can be added for the purpose of accelerating the reaction. Examples of the catalyst include a potassium or a sodium salt of alkylphosphonic acid, metal salts such as a sodium salt, a potassium salt, a nickel salt, a cobalt salt, a cadmium salt, a barium salt, a calcium salt, and a zinc salt of fatty acids having 8 to 20 carbon atoms, and organic tin compounds such as dibutyl tin dilaurate, dioctyl tin maleate, dibutyl dibutoxy tin, bis(2-ethylhexyl) tin oxide, and 1,1,3,3-tetrabutyl-1,3-diacetoxydistannoxane, and tert-amine compounds such as N,N,N',N'',N''-pentamethyl diethylene triamine (PMDETA), N,N,N',N'',N''-pentamethyl-(3-aminopropyl)ethylenediamine, N,N,N',N'',N''-pentamethyl dipropylene triamine, N,N,N',N'-tetramethylguanidine, 1,3,5-tris (N,N-dimethylaminopropyl)hexahydro-S-triazine, 1,8-diazabicyclo [5.4.0]undecene-7, N,N'-dimethylpiperazine, N,N-dimethylcyclohexylamine, N-methyldicyclohexyl amine, N,N,N',N'-tetramethylpropylenediamine, N,N,N',N'-tetramethyl hexamethylenediamine, N-ethyl morpholine (NEM), N-methyl morpholine, N,N-dimethyl ethanolamine (DMEA), N,N-diethyl ethanolamine, dimethylaminopropyl amine, dimorpholinodiethyl ether (DMDEE), bis(2-dimethylaminoethyl) ether, 1-methylimidazole, 1,2-dimethyl imidazole, 1-isobutyl-2-methylimidazole, 1-dimethylaminopropyl imidazole, or triethylenediamine (TED). They may be used either singly or in combination of two or more kinds thereof. The use amount of the catalyst is preferably usually 1% by weight or less, and more preferably 0.1% by weight or less, relative to the total weight of the raw material components.

In order to suppress radical polymerization of the (meth)acrylamide containing hydroxyl group during urethanization, a radical polymerization inhibitor can be used as necessary. Examples of the radical polymerization inhibitor include quinone based polymerization inhibitors such as hydroquinone, methoxyhydroquinone, benzoquinone and p-tert-butylcatechol; alkyl phenol based polymerization inhibitors such as 2,6-di-tert-butylphenol, 2,4-di-tert-butylphenol, 2-tert-butyl 4,6-dimethylphenol, 2,6-di-tert-butyl-4-methylphenol and 2,4,6-tri-tert-butylphenol; amine based polymerization inhibitors such as alkylated diphenylamine, N,N'-diphenyl-p-phenylenediamine, and phenothiazine, and N-oxyls such as 4-hydroxy-2,2,6,6-tetramethylpiperidine-N-oxyl; and copper dithiocarbamate based polymerization inhibitors such as copper dimethyl dithiocarbamate, copper diethyl dithiocarbamate and copper dibutyl dithiocarbamate. They may be used either singly two or more types thereof may be used in combination.

The addition amount of these polymerization inhibitors may be suitably set depending on the kind, the blending amount or the like of the (meth)acrylamide having a hydroxyl group. From the viewpoint of polymerization suppressing effects, convenience in production, and economic efficiency, the addition amount is preferably usually 0.001 to 5% by weight, and more preferably 0.01 to 1% by weight, relative to the total weight of the raw materials for urethanization.

The number average molecular weight of the (meth) acrylamide based urethane oligomer of the present invention is preferably 4,500 to 50,000, and more preferably 4,500 to 30,000. When the number average molecular weight is less than 4,500, there is possibility to have lower solubility and poor transparency when it is prepared as a resin composition. On the other hand, when the molecular weight is less than 500, low molecular weight components, in particular, the aforementioned urethane adduct compound, are contained in a large amount. Due to such reasons, the resin composition composed of the oligomer has even poorer transparency. The adhesion property and water resistance of a coating film to be obtained are also deteriorated. On the other hand, when the number average molecular weight is more than 30,000, high viscosity is yielded, and thus the handlability is impaired. Due to such reasons, the number average molecular weight of more than 30,000 is not desirable. In particular, when the number average molecular weight is 4,500 or more, the (meth)acrylamide based urethane oligomer having an ether skeleton and an ester skeleton shows a tendency of having significantly enhanced moisture resistance and adhesion property for various substrates, and thus desirable.

The acryl equivalents of the (meth)acrylamide based urethane oligomer of the present invention are preferably 750 to 25,000. When the acryl equivalents are less than 750, higher curing rate is yielded. However, there is a possibility that the curing shrinkage is not fully suppressed within a range of 5%. Due to such reasons, the acryl equivalents of less than 750 are not desirable. On the other hand, when the acryl equivalents is more than 25,000, there is a possibility that the active energy ray curing property and strength or water resistance of a cured film are lowered by the presence of a non-polymerizable compound.

Viscosity of the (meth)acrylamide based urethane oligomer of the present invention is preferably 500,000 mPa·s or less, and more preferably 300,000 mPa·s or less at 60° C. If the viscosity at 60° C. is higher than 500,000 mPa·s, there is a possibility of having poor handlability due to the loss of fluidity during operation. Thus, the viscosity higher than 500,000 mPa·s is not desirable.

An active energy ray curable resin composition can be prepared by using the (meth)acrylamide based urethane oligomer of the present invention alone or by mixing with other active energy ray curable monomer or oligomer. When the (meth)acrylamide based urethane oligomer of the present invention is used alone, the physical properties like curing property of a resin composition, water absorption ratio, strength, and elongation of an obtained cured product, which vary depending on the polyol skeleton, type and number of the (meth)acrylamide group, and molecular weight of the oligomer, are preferably within the following range, in general.

The (meth)acrylamide based urethane oligomer of the present invention can be completely cured by irradiation with active energy rays. The active energy ray irradiation amount required (cumulative amount of light) varies depending on the type of (meth)acrylamide group of the urethane oligomer. The cumulative amount of light is preferably 10 to 2,000 mJ/cm$^2$, and particularly preferably about 100 to 1000 mJ/cm$^2$. If the cumulative amount of light is less than 10 mJ/cm$^2$, insufficiently cured portions remain, and, as a result, there is a possibility that the overall strength, elongation, and water resistance of a cured product deteriorate. In addition, if the cumulative amount of light is greater than 2,000 mJ/cm$^2$, side reactions such as decomposition occur due to excess energy, and there is a tendency that the cured film is easily colored.

The water absorption ratio of a cured film formed of the (meth)acrylamide based urethane oligomer of the present invention is preferably 5% or less, and particularly preferably 2% or less. If the water absorption ratio is greater than 5%, in the case of using for a long period of time under a high humidity environment, water absorption by the cured film occurs over time. As a result, distortion of the shape occurs as caused by expansion. As a result, there is a possibility of having a deterioration of the adhesion property and transparency.

Strength (tensile strength at break) and elongation (tensile elongation at break) of a cured film which is formed of the (meth)acrylamide based urethane oligomer of the present invention is preferably 0.5 to 40 MPa and 5 to 300%, respectively. The strength and elongation of the (meth) acrylamide based urethane oligomer can be within those ranges. Due to such reasons, the active energy ray curable resin composition consisting of a mixture of other active energy ray curable monomers and oligomers can be used for various kinds of fields including cohesives, adhesives, coatings, ink composition, sealing agent, a composition for nail decoration, an agent for protecting car exteriors, and a curable composition for decorative film or the like.

For a photocurable resin composition for an electronic device, the urethane oligomer of the present invention can be naturally used alone. For the purpose of the adjusting the curing property and fluidity of the resin composition, and also the physical property values like water resistance, flexibility, and cohesive property of a cured product to be obtained, the urethane oligomer of the present invention may be used after mixing it with other photocurable monomer or oligomer. The blending amount of the urethane oligomer in a photocurable resin composition to be used is preferably 1% by weight or more, and more preferably 10 to 60% by weight. When the urethane oligomer is less than 1% by weight, there is a possibility that the function like curing property and low curing shrinkage property is not provided sufficiently. Furthermore, as for an example of the monomer and oligomer which can be used in combination with the urethane oligomer, monofunctional (meth)acrylate and/or monofunctional (meth)acrylamide, polyfunctional (meth) acrylate and/or polyfunctional (meth)acrylamide can be mentioned. The monomer or oligomer may be used either singly or in combination of two or more kinds thereof. Furthermore, if necessary, it may include a polymerizable quaternary salt ion liquid.

Examples of the monofunctional (meth)acrylate which is used in the present invention include alkyl (meth)acrylate such as methyl (meth)acrylate, hydroxyethyl acrylate, alkoxyethyl (meth)acrylate, methoxy diethylene glycol (meth)acrylate, 2-(2-ethoxyethoxy)ethyl acrylate, phenoxyethyl (meth)acrylate, cyclohexyl (meth)acrylate, benzyl (meth)acrylate, phenoxyethyl (meth)acrylate, dicyclopentanyl (meth)acrylate, isobornyl (meth)acrylate, tetrahydrofurfuryl acrylate, 2-methyl-2-adamantyl (meth)acrylate, allyl (meth)acrylate, and hydroxyalkyl (meth)acrylate such as hydroxyethyl (meth)acrylate. Those monofunctional acrylates may be used either singly or in combination of two or more kinds thereof.

Examples of the monofunctional (meth)acrylamide which is used in the present invention include N-methyl (meth) acrylamide, N-ethyl (meth)acrylamide, N-methoxymethyl (meth)acrylamide, N-ethoxy methyl (meth)acrylamide, N-methoxyethyl (meth)acrylamide, N-ethoxyethyl (meth)acrylamide, N-n-butoxymethyl (meth)acrylamide, N-isobutoxymethyl (meth)acrylamide, N-vinylpyrrolidone, N-vinylcaprolactam, N-(2-hydroxyethyl)acrylamide, N-[3-(dimethylamino)]propyl acrylamide, N,N-dimethyl (meth)acrylamide, N,N-diethyl (meth)acrylamide, N-acryloyl morpholine, and hydroxyalkyl (meth)acrylamide such as hydroxyethyl acrylamide. Those monofunctional acrylamides may be used either singly or in combination of two or more kinds thereof.

Examples of the polyfunctional (meth)acrylate include monomers and oligomers of ethylene glycol di(meth)acrylate, diethylene glycol di(meth)acrylate, propylene glycol di(meth)acrylate, tripropylene glycol di(meth)acrylate, di tetraethylene glycol di(meth)acrylate, polyethylene glycol di(meth)acrylate, polypropylene glycol di(meth)acrylate, polytetramethylene glycol di(meth)acrylate, 1,3-butane diol di(meth)acrylate, 1,4-butane diol di(meth)acrylate, neopentyl glycol di(meth)acrylate, 1,6-hexane diol di(meth)acrylate, 1,7-heptane diol di(meth)acrylate, 1,8-octane diol di(meth)acrylate, 1,9-nonane diol di(meth)acrylate, hydroxy pivalic acid neopentyl glycol di(meth)acrylate, dicyclopentanyl di(meth)acrylate, caprolactone-modified dicyclopentenyl di(meth)acrylate, ethylene oxide-modified phosphoric acid di(meth)acrylate, pentaerythritol tetra (meth)acrylate, pentaerythritol tri(meth) acrylate, dipentaerythritolhexa(meth)acrylate, dipentaerythritol penta (meth)acrylate, dipentaerythritol tetra (meth)acrylate, trimethylol ethane tri(meth) acrylate, trimethylol propane tri(meth) acrylate, tricyclodecane dimethanol di(meth)acrylate, ethylene oxide-modified bisphenol A di(meth)acrylate, propylene oxide-modified bisphenol A di(meth)acrylate, cyclohexane dimethanol di(meth)acrylate, acrylate ester (dioxane glycol diacrylate), alkoxylated hexane diol di(meth)acrylate, alkoxylated (cyclo)hexane dimethanol di(meth)acrylate, epoxy (meth)acrylate, and urethane (meth)acrylate. Furthermore, those polyfunctional (meth)acrylates may be used either singly or two or more kinds thereof may be used in combination.

Examples of the polyfunctional (meth)acrylamide include methylene bis (meth)acrylamide, ethylene bis (meth)acrylamide, and diallyl (meth)acrylamide. Furthermore, those polyfunctional (meth)acrylamides may be used either singly or two or more kinds thereof may be used in combination.

Furthermore, as component (F), an organic ionic compound may be blended. Examples of the organic ionic compound include an ionic vinyl monomer and/or an oligomer and a polymer which include the monomer as a constitutional unit. The ionic vinyl monomer is an onium salt obtained by combining a cation and an anion. Specific examples of the cation include (meth)acrylate based or (meth)acrylamide based ammonium ions and imidazolium ions. Examples of the anions include halogen ions such as $Cl^-$, $Br^-$ and $I^-$, inorganic acid anions or organic acid anions such as $OH^-$, $CH_3COO^-$, $NO_3^-$, $ClO_4^-$, $PF_6^-$, $BF_4^-$, $HSO_4^-$, $CH_3SO_3^-$, $CF_3SO_3^-$, $CH_3C_6H_6SO_3^-$, $C_4F_9SO_3^-$, $(CF_3SO_2)_2N^-$, and $SCN^-$.

As a general example of a method for synthesizing a polymerizable quaternary salt ion liquid that is used in the present invention, a method of quaternizing a tertiary amine having a polymerizable group with a quaternizing agent such as alkyl halide, dialkyl sulfate or methyl p-toluenesulfonate, a method of performing anion exchange on the quaternary ammonium salt obtained by quaternization using a salt having a desired anion, and a method of converting a quaternary ammonium salt to hydroxide using an anion exchange resin and then neutralizing with an acid having a desired anion can be mentioned.

Ions of a polymerizable quaternary salt ion liquid easily form a hydrogen bond and an ionic bond with a coating substrate, and they can impart conductivity or antistatic properties. As a result, wettability is improved. Due to such reasons, it is possible to achieve more uniform application, and as a result, a film can be formed more stably. Furthermore, since a polymerizable quaternary salt ion liquid itself is also an active energy ray curable compound, and thus, by copolymerizing it with the active energy ray curable resin composition of the present invention, it is possible to provide auxiliary effects of permanently imparting conductivity or antistatic properties without bleed out. Furthermore, an effect of enhancing the adhesion property is also provided.

The polymerizable quaternary salt ion liquid can be used in combination of one type or as necessary, two or more types selected from monomolecular compounds having a molecular weight of several tens to several hundreds, oligomers having a molecular weight of several hundreds to several thousands and polymers having a molecular weight of several thousands to tens of thousands. The blending amount of the polymerizable quaternary salt ion liquid can be adjusted by the number of functional groups and the molecular weight of the ion pair, and thus, is not particularly limited. In general, the addition amount of the polymerizable quaternary salt ion liquid is preferably 0 to 50% by weight, and particularly preferably 0 to 10% by weight, relative to the urethane oligomer of the present invention. If the blending amount of the polymerizable quaternary salt ion liquid is greater than 50% by weight, there is a possibility that the deterioration of transparency of a cured film occurs depending on the type of the polymerizable quaternary salt ion liquid.

The active energy ray of the present invention is defined as energy rays which can generate an active species by decomposing a compound (photopolymerization initiator) which generates an active species. Examples of such an active energy rays include light energy rays such as visible light, an electron beam, ultraviolet rays, infrared rays, X-rays, α-rays, β-rays, and γ-rays.

When curing the active energy ray curable resin composition of the present invention, a photopolymerization initiator is added in advance. However, the photopolymerization initiator is not particularly necessary in the case of using an electron beam as an active energy ray. However, the photopolymerization initiator will be necessary when ultraviolet ray is employed. The photopolymerization initiator may be suitably selected from usual ones such as an acetophenone based photopolymerization initiator, a benzoin based photopolymerization initiator, a benzophenone based photopolymerization initiator and a thioxanthone based photopolymerization initiator. Among the photopolymerization initiators, as commercially available products, Irgacure 1173, Irgacure 184, Irgacure 369, Irgacure 500, Irgacure 651, Irgacure 754, Irgacure 819, Irgacure 907, Irgacure 2959, Irgacure TPO manufactured by BASF SE, and product name Ubecryl P36 manufactured by UCB Chemicals can be used. Those photopolymerization initiators may be used either one or two or more kinds thereof may be used in combination.

The amount of the photopolymerization initiator used is not particularly limited, and in general, 0.1 to 10% by weight is added, and 1 to 5% by weight is preferably added, relative to the active energy ray curable resin composition. If the amount is less than 0.1% by weight, a sufficient curing property is not obtained, and if the amount is greater than 10% by weight, there is a possibility that deterioration of the strength or yellowing of the coating film occurs.

In a range in which the characteristics of the active energy ray curable resin composition of the present invention and the molded article produced using the composition are not impaired, other arbitrary component such as a pigment, a dye, a surfactant, an antiblocking agent, a leveling agent, a dispersant, a defoamer, an antioxidant, an ultraviolet sensitizer or a preservative may be used in combination.

The active energy ray curable resin composition of the present invention applied to the surface of a substrate or between substrates, such as paper, fabric, nonwoven fabric, glass, plastics including polyethylene terephthalate, diacetate cellulose, triacetate cellulose, an acrylic polymer, polyvinyl chloride, cellophane, celluloid, polycarbonate and polyimide, and metals can be cured by irradiation with an active energy rays like ultraviolet ray. Accordingly, it is possible to obtain a coating layer or an ink layer, a cohesive layer or an adhesive layer, each having high performance. As the method of applying this usable resin composition on a substrate, a normal coating film formation method such as a spin coating method, a spray coating method, a dipping method, a gravure roll method, a knife coating method, a reverse roll method, a screen printing method, or a bar coater method can be mentioned. In addition, as the method of application between substrates, a lamination method, a roll-to-roll method, and the like can be mentioned.

EXAMPLES

Hereinbelow, the present invention is described in detail and more specifically with reference to Synthesis Examples and Evaluation Examples, but the present invention is not limited to the examples. Furthermore, in the followings, % other than yield indicates % by weight. Physical property analysis of the obtained urethane oligomer was performed by the following methods.

(1) Measurement of Molecular Weight

The number average molecular weight of the obtained urethane oligomer and content of a urethane adduct compound were measured by high-performance liquid chromatography ("LC-10A" manufactured by Shimadzu Corporation, column: Shodex GPC KF-806L (exclusion limit molecular weight: $2\times10^7$, separation range: 100 to $2\times10^7$, theoretical plate number: 10,000 plates/piece (set), filler material: styrene-divinylbenzene copolymer, filler particle size: 10 μm), eluent: tetrahydrofuran) and calculated by a standard polystyrene molecular weight conversion method.

(2) Measurement of Viscosity

By using a cone-plate type viscometer (device name: "RE550 viscometer" manufactured by Toki Sangyo Co., Ltd.), the viscosity the urethane oligomer which has been obtained from each Synthetic example or Comparative synthetic example was measured at 60° C. according to JIS K5600-2-3.

Synthesis Example 1

Synthesis of Urethane Oligomer UT-1

Into a 500 mL four-neck flask provided with a stirrer, a thermometer, a condenser and a dry gas inlet tube, 16.2 g (73.1 mmol) of isophorone diisocyanate (IPDI) and 0.1 g of dibutyl tin dilaurate were added. Then, while performing flushing with dry nitrogen, 189.0 g (62.8 mmol) of UT-1001 (acryl polymer, manufactured by Soken Chemical & Engineering Co., Ltd., number average molecular weight: 3500) was added dropwise thereto while adjusting the dropwise addition rate such that the temperature is maintained at 80° C., and the reaction was allowed to occur for 3 hours at 80° C. Next, after cooling the reaction solution to 40° C., 0.2 g of methyl hydroquinone (MHQ) was added thereto. Bubbling with dry air was carried out for 10 minutes. Then, after adding 5.42 g (45.6 mmol) of hydroxyethyl methacrylamide (HEMAA), under a dry air stream, stirring was continued for 5 hours while maintaining the temperature in the system at 80° C. As a result, 188.16 g of UT-1 was obtained as pale yellow liquid with viscosity. The yield was 96.5%.

An analysis was carried out by using an infrared absorption spectrum (IR). It was found that the absorption (2250 $cm^{-1}$) specific to the isocyanate group of IPDI as a raw material is completely lost. Furthermore, specific absorption (1,650 $cm^{-1}$) of the amide group derived from "HEAA" and specific absorption (1,740 $cm^{-1}$) of the urethane bond generated were detected. Accordingly, generation of a target urethane oligomer UT-1 was confirmed. The number average molecular weight of the obtained urethane oligomer UT-1 was 11,600. The viscosity at 60° C. was found to be 25,100 mPa·s, and the low molecular weight component contained therein was 1.5%.

Synthesis Example 2

Synthesis of Urethane Oligomer UT-2

The same apparatus as that of Synthesis Example 1 was used. 11.4 g (67.8 mmol) of hexamethylene diisocyanate (HDI) and 0.06 g of dibutyl tin dilaurate were added. Then, while performing flushing with dry nitrogen, 100.0 g (50.0 mmol) of UNIOL D-2000 (polypropylene glycol, manufactured by NOF Corporation, number average molecular weight: 2000) was added dropwise thereto while adjusting the dropwise addition rate such that the temperature is maintained at 70° C., and the reaction was allowed to occur for 4 hours at 70° C. Next, after cooling the reaction solution to 40° C., 0.06 g of MHQ was added thereto. Bubbling with dry air was carried out for 10 minutes. Then, 1.88 g (16.4 mmol) of HEAA and 0.52 g (16.4 mmol) of methanol (manufactured by Wako Pure Chemical Industries, Ltd.) were added. Under a dry air stream, stirring was continued for 3 hours while maintaining the temperature in the system at 80° C. As a result, 111.80 g of UT-2 was obtained as pale yellow liquid with viscosity. The yield was 98.2%. Similar to Synthesis Example 1, generation of a target urethane oligomer UT-2 was confirmed by an IR analysis. The number average molecular weight of the obtained urethane oligomer UT-2 was 6,800. The viscosity at 60° C. was found to be 12,000 mPa·s, and the low molecular weight component contained therein was 0.4%.

Synthesis Example 3

Synthesis of Urethane Oligomer UT-3

The same apparatus as that of Synthesis Example 1 was used. 10.0 g (5.00 mmol) of PTMG2000 (polytetramethylene glycol, manufactured by Mitsubishi Chemical Corporation, number average molecular weight: 2000), 90.0 g (45.0 mmol) of UNIOL D-2000, and 0.06 g of dibutyl tin dilaurate were added. Then, while performing flushing with dry nitrogen, 14.8 g (58.0 mmol) of dicyclohexylmethane 4,4'-diisocyanate (hydrogenated MDI) was added dropwise thereto while adjusting the dropwise addition rate such that the temperature is maintained at 90° C., and the reaction was allowed to occur for 2 hours at 90° C. Next, after cooling the reaction solution to 40° C., 0.2 g of MHQ was added thereto.

Bubbling with dry air was carried out for 10 minutes. Then, 3.20 g (27.8 mmol) of HEAA was added. Under a dry air stream, stirring was continued for 3 hours while maintaining the temperature in the system at 90° C. As a result, 112.00 g of UT-3 was obtained as pale yellow liquid with viscosity. The yield was 96.8%. Similar to Synthesis Example 1, generation of a target urethane oligomer UT-3 was confirmed by an IR analysis. The number average molecular weight of the obtained urethane oligomer UT-3 was 18,500. The viscosity at 60° C. was found to be 25,600 mPa·s, and the low molecular weight component contained therein was 0.7%.

Synthesis Example 4

Synthesis of Urethane Oligomer UT-4

The same apparatus as that of Synthesis Example 1 was used. 150.0 g (50.0 mmol) of UNIOL D-3000 (polypropylene glycol, manufactured by NOF Corporation, number average molecular weight: 3000) and 1.88 g (6.25 mmol) of ADEKA EDP-300 (polyether polyol, manufactured by ADEKA Corporation, number average molecular weight: 300) were dissolved in 200 g of dehydrated acetone followed stirring for 30 minutes. Then, 16.8 g (75.8 mmol) of IPDI was added thereto and additionally stirred for 30 minutes. Under a dry air stream, temperature of the reaction solution was raised to 65° C. After that, 0.08 g of dibutyl tin dilaurate and 0.2 g of MHQ was added thereto and the reaction was allowed to occur at 2 hours. Then, 4.88 g (37.8 mmol) of N-methyl hydroxyethyl acrylamide (MHEAA) was added thereto. Under a dry air stream, stirring was continued for 3 hours while maintaining the temperature in the system at 60° C. After that, the acetone was removed by a drying process under reduced pressure, and as a result, 166.36 g of UT-4 was obtained as transparent liquid with viscosity. The yield was 97.0%. Similar to Synthesis Example 1, generation of a target urethane oligomer UT-4 was confirmed by an IR analysis. The number average molecular weight of the obtained urethane oligomer UT-4 was 27,000. The viscosity at 60° C. was found to be 40,000 mPa·s, and the low molecular weight component contained therein was 0.2%.

Synthesis Example 5

Synthesis of Urethane Oligomer UT-5

The same apparatus as that of Synthesis Example 1 was used. 85.0 g (50.0 mmol) of KF-6001 (silicone polyol, manufactured by Shin Etsu Chemical Co., Ltd., number average molecular weight: 1700) and 0.05 g of dibutyl tin dilaurate were added. Then, while performing flushing with dry nitrogen, 12.5 g (56.5 mmol) of IPDI was added dropwise thereto while maintaining the temperature at 80° C., and the reaction was allowed to occur additionally for 4 hours at 80° C. Next, similar to Synthesis Example 1, 0.2 g of MHQ and 1.50 g (12.7 mmol) of "HEAA" were added thereto and stirring was continued for 3 hours at 80° C. As a result, 96.10 g of UT-5 was obtained as pale yellow liquid with viscosity. The yield was 96.8%. Generation of a target urethane oligomer UT-5 was confirmed by an IR analysis. The weight average molecular weight of the obtained UT-5 was 15,600. The viscosity at 60° C. was found to be 47,500 mPa·s, and the low molecular weight component contained therein was 0.4%.

Synthesis Example 6

Synthesis of Urethane Oligomer UT-6

The same apparatus as that of Synthesis Example 1 was used. 60.0 g (20.0 mmol) of ADEKA NewAce Y6-30 (polyester diol manufactured by Asahi Kasei Corporation, number average molecular weight: 3000), 30.0 g (30.0 mmol) of UNIOL D-1000, and 0.05 g of dibutyl tin dilaurate were added. Then, while performing flushing with dry nitrogen, 9.10 g (54.0 mmol) of HDI was added dropwise thereto while adjusting the dropwise addition rate such that the temperature is maintained at 80° C., and the reaction was allowed to occur for 4 hours at 80° C. Next, after cooling the reaction solution to 40° C., 0.2 g of MHQ was added thereto. Bubbling with dry air was carried out for 10 minutes. Then, 0.50 g (4.30 mmol) of "HEAA" was added. Under a dry air stream, stirring was continued for 5 hours while maintaining the temperature in the system at 60° C. As a result, 97.30 g of UT-6 was obtained as pale yellow liquid with viscosity. The yield was 97.3%. Similar to Synthesis Example 1, generation of a target urethane oligomer UT-6 was confirmed by an IR analysis. The number average molecular weight of the obtained urethane oligomer UT-6 was 46,000. The viscosity at 60° C. was found to be 93,000 mPa·s, and the low molecular weight component contained therein was 0.3%.

Synthesis Example 7

Synthesis of Urethane Oligomer UT-7

The same apparatus as that of Synthesis Example 1 was used. 60.0 g (30.0 mmol) of SONGSTAR (tm) SS-2077 (polyester polyol manufactured by SONGWON, number average molecular weight of 1850 to 2350), 20.0 g (20.0 mmol) of UNIOL D-1000, and 0.06 g of dibutyl tin dilaurate were added. Then, while performing flushing with dry nitrogen, 9.70 g (54.0 mmol) of HDI was added dropwise thereto while adjusting the dropwise addition rate such that the temperature is maintained at 80° C., and the reaction was allowed to occur for 4 hours at 80° C. Next, after cooling the reaction solution to 40° C., 0.2 g of MHQ was added thereto. Bubbling with dry air was carried out for 10 minutes. Then, 2.19 g (17.0 mmol) of "HEAA" was added. Under a dry air stream, stirring was continued for 5 hours while maintaining the temperature in the system at 60° C. As a result, 87.90 g of UT-7 was obtained as pale yellow liquid with viscosity. The yield was 96.3%. Similar to Synthesis Example 1, generation of a target urethane oligomer UT-7 was confirmed by an IR analysis. The number average molecular weight of the obtained urethane oligomer UT-7 was 21,400. The viscosity at 60° C. was found to be 90,000 mPa·s, and the low molecular weight component contained therein was 0.2%.

Synthesis Example 8

Synthesis of Urethane Oligomer UT-8

Into a 500 mL four-neck flask provided with a stirrer, a thermometer, a condenser and a dry gas inlet tube, 14.0 g (66.5 mmol) of trimethylhexamethylene diisocyanate (TMDI) and 0.06 g of dibutyl tin dilaurate were added. Then, while performing flushing with dry nitrogen, 80.0 g (40.0 mmol) of P-2012 (polyester polyol, manufactured by Kuraray Co., Ltd., number average molecular weight: 2000) and 10.0 g (10 mmol) of P-1010 (polyester polyol, manufactured by Kuraray Co., Ltd., number average molecular weight: 1000) were added dropwise thereto while adjusting the dropwise addition rate such that the temperature is maintained at 80° C., and the reaction was allowed to occur for 3 hours at 80° C. Next, after cooling the reaction solution to 40° C., 0.2 g of methyl hydroquinone (MHQ) was added thereto. Bubbling with dry air was carried out for 10 minutes. Then, after adding 7.46 g (57.9 mmol) of hydroxyethyl acrylamide (HEAA), under a dry air stream, stirring was continued for 5 hours while maintaining the temperature in the system at 80° C. As a result, 107.5 g of UT-8 was obtained as pale yellow liquid with viscosity. The yield was 96.5%. An analysis was carried out by using an infrared absorption spectrum (IR). It was found that the absorption (2250 cm$^{-1}$) specific to the isocyanate group of IPDI as a raw material is completely lost. Furthermore, specific absorption (1650 cm$^{-1}$) of the amide group derived from "HEAA" and specific absorption (1740 cm$^{-1}$) of the urethane bond generated were detected. Accordingly, generation of a target urethane oligomer UT-8 was confirmed. The number average molecular weight of the obtained urethane oligomer UT-8 was 6,240. The viscosity at 60° C. was found to be 267,000 mPa·s, and the low molecular weight component contained therein was 0.1%.

Synthesis Example 9

Synthesis of Urethane Oligomer UT-9

The same apparatus as that of Synthesis Example 1 was used. 70.0 g (35.0 mmol) of P-2010 (polyester polyol, manufactured by Kuraray Co., Ltd., number average molecular weight: 2000), 27.0 g (15.0 mmol) of KF6001 (silicone polyol, manufactured by Shin Etsu Chemical Co., Ltd., number average molecular weight: 1700), and 0.06 g of dibutyl tin dilaurate were added. Then, while performing flushing with dry nitrogen, 11.8 g (56.3 mmol) of TMDI was added dropwise thereto while adjusting the dropwise addition rate such that the temperature is maintained at 80° C., and the reaction was allowed to occur for 4 hours at 80° C. Next, after cooling the reaction solution to 40° C., 0.2 g of MHQ was added thereto. Bubbling with dry air was carried out for 10 minutes. Then, 2.17 g (16.78 mmol) of "HEAA" was added. Under a dry air stream, stirring was continued for 5 hours while maintaining the temperature in the system at 60° C. As a result, 107.90 g of UT-9 was obtained as pale yellow liquid with viscosity. The yield was 97.2%. Similar to Synthesis Example 1, generation of a target urethane oligomer UT-9 was confirmed by an IR analysis. The number average molecular weight of the obtained urethane oligomer UT-9 was 17,410. The viscosity at 60° C. was found to be 150,000 mPa·s, and the low molecular weight component contained therein was 0.1%.

Synthesis Example 10

Synthesis of Urethane Oligomer UT-10

The same apparatus as that of Synthesis Example 1 was used. 50.0 g (25.0 mmol) of P-2010 (polyester polyol, manufactured by Kuraray Co., Ltd., number average molecular weight: 2000), 87.5 g (25.0 mmol) of UT-1001 (acryl polymer, manufactured by Soken Chemical & Engineering Co., Ltd., number average molecular weight: 3500), and 0.06 g of dibutyl tin dilaurate were added. Then, while performing flushing with dry nitrogen, 14.8 g (66.5 mmol) of isophorone diisocyanate (IPDI) was added dropwise thereto while adjusting the dropwise addition rate such that the temperature is maintained at 80° C., and the reaction was allowed to occur for 4 hours at 80° C. Next, after cooling the reaction solution to 40° C., 0.2 g of MHQ was added thereto. Bubbling with dry air was carried out for 10 minutes. Then, 5.98 g (46.4 mmol) of "HEAR" was added. Under a dry air stream, stirring was continued for 5 hours while maintaining the temperature in the system at 60° C. As a result, 155.10 g of UT-10 was obtained as pale yellow liquid with viscosity. The yield was 98.0%. Similar to Synthesis Example 1, generation of a target urethane oligomer UT-10 was confirmed by an IR analysis. The number average molecular weight of the obtained urethane oligomer UT-10 was 9,100. The viscosity at 60° C. was found to be 70,000 mPa·s, and the low molecular weight component contained therein was 0.2%.

Synthesis Example 11

Synthesis of Urethane Oligomer UT-11

The same apparatus as that of Synthesis Example 1 was used. 90.0 g (45.0 mmol) of P-2012 (polyester polyol, manufactured by Kuraray Co., Ltd., number average molecular weight: 2000), 0.4 g (4.0 mmol) of UNIOL D-1000 (polypropylene glycol, manufactured by NOF Corporation, number average molecular weight: 1000), 0.1 g (0.18 mmol) of KF-6001, and 0.97 g (3.22 mmol) of ADEKA EDP-300 (polyether polyol, manufactured by ADEKA Corporation, number average molecular weight: 300) were dissolved in 200 g of dehydrated acetone followed stirring for 30 minutes. Then, 16.1 g (72.5 mmol) of IPDI was added thereto and additionally stirred for 30 minutes. Under a dry air stream, temperature of the reaction solution was raised to 65° C. After that, 0.08 g of dibutyl tin dilaurate and 0.2 g of MHQ were added thereto and the reaction was allowed to occur at 2 hours. Then, 2.75 g (23.9 mmol) of "HEAA" was added thereto. Under a dry air stream, stirring was continued for 3 hours while maintaining the temperature in the system at 60° C. After that, the acetone was removed by a drying process under reduced pressure, and as a result, 105.10 g of UT-11 was obtained as transparent liquid with viscosity. The yield was 96.1%. Similar to Synthesis Example 1, generation of a target urethane oligomer UT-11 was confirmed by an IR analysis. The number average molecular weight of the obtained urethane oligomer UT-11 was 36,700. The viscosity at 60° C. was found to be 475,000 mPa·s, and the low molecular weight component contained therein was 0.2%.

Synthesis Example 12

Synthesis of Urethane Oligomer UT-12

The same apparatus as that of Synthesis Example 1 was used. 20.0 g (50.0 mmol) of ADEKA Polyether P-400 and 0.02 g of dibutyl tin dilaurate were added. Then, while performing flushing with dry nitrogen, 24.6 g (60.0 mmol) of DESMODUL XP2580 (alophanate group-containing polyisocyanate manufactured by Sumika Bayer Urethane Co., Ltd.) was added dropwise thereto while adjusting the dropwise addition rate such that the temperature is maintained at 80° C., and the reaction was allowed to occur for 4 hours at 80° C. Next, after cooling the reaction solution to 40° C., 0.2 g of MHQ was added thereto. Bubbling with dry air was carried out for 10 minutes. Then, 1.06 g (9.21 mmol)

of "HEAA" was added. Under a dry air stream, stirring was continued for 5 hours while maintaining the temperature in the system at 60° C. As a result, 28.25 g of UT-12 was obtained as pale yellow liquid with viscosity. The yield was 98.2%. Similar to Synthesis Example 1, generation of a target urethane oligomer UT-12 was confirmed by an IR analysis. The number average molecular weight of the obtained urethane oligomer UT-12 was 4,690. The viscosity at 60° C. was found to be 15,000 mPa·s, and the low molecular weight component contained therein was 0.5%.

Synthesis Example 13

Synthesis of Urethane Oligomer UT-13

The same apparatus as that of Synthesis Example 1 was used. 10.0 g (45.0 mmol) of PEG-200 (polyethylene glycol, manufactured by ADEKA Corporation, number average molecular weight: 200) and 1.88 g (6.25 mmol) of ADEKAE DP-300 (polyether polyol, manufactured by ADEKA Corporation, number average molecular weight: 300) were dissolved in 200 g of dehydrated acetone followed stirring for 30 minutes. Then, 24.6 g (60.0 mmol) of DESMODUL XP2580 (alophanate group-containing polyisocyanate manufactured by Sumika Bayer Urethane Co., Ltd.) was added thereto and additionally stirred for 30 minutes. Under a dry air stream, temperature of the reaction solution was raised to 65° C. After that, 0.08 g of dibutyl tin dilaurate and 0.2 g of MHQ were added thereto and the reaction was allowed to occur at 2 hours. Then, 1.27 g (13.0 mmol) of "HEAA" was added thereto. Under a dry air stream, stirring was continued for 3 hours while maintaining the temperature in the system at 60° C. After that, the acetone was removed by a drying process under reduced pressure, and as a result, 23.60 g of UT-13 was obtained as transparent liquid with viscosity. The yield was 97.9%. Similar to Synthesis Example 1, generation of a target urethane oligomer UT-13 was confirmed by an IR analysis. The number average molecular weight of the obtained urethane oligomer UT-13 was 7,300. The viscosity at 60° C. was found to be 20,000 mPa·s, and the low molecular weight component contained therein was 0.8%.

Synthesis Example 14

Synthesis of Urethane Oligomer UT-14

The same apparatus as that of Synthesis Example 1 was used. 25.0 g (25.0 mmol) of ETERNACOLL UC-100 (polyester polyol, manufactured by Kuraray Co., Ltd., number average molecular weight: 1000), 25.0 g (25.0 mmol) of UNIOL D-1000, and 0.03 g of dibutyl tin dilaurate were added. Then, while performing flushing with dry nitrogen, 13.9 g (62.5 mmol) of IPDI was added dropwise thereto while adjusting the dropwise addition rate such that the temperature is maintained at 80° C., and the reaction was allowed to occur for 4 hours at 80° C. Next, after cooling the reaction solution to 40° C., 0.2 g of MHQ was added thereto. Bubbling with dry air was carried out for 10 minutes. Then, 1.53 g (13.3 mmol) of "HEAA" was added. Under a dry air stream, stirring was continued for 5 hours while maintaining the temperature in the system at 60° C. As a result, 58.70 g of UT-14 was obtained as pale yellow liquid with viscosity. The yield was 98.6%. Similar to Synthesis Example 1, generation of a target urethane oligomer UT-14 was confirmed by an IR analysis. The number average molecular weight of the obtained UT-14 was 5,300. The viscosity at 60° C. was found to be 23,000 mPa·s, and the low molecular weight component contained therein was 0.1%.

Synthesis Example 15. Synthesis of Urethane Oligomer UT-15

The same apparatus as that of Synthesis Example 1 was used. 50.0 g (25.0 mmol) of ETERNACOLL UHC-50-200 (polyester polyol, manufactured by Kuraray Co., Ltd., number average molecular weight: 2000), 25.0 g (25.0 mmol) of KURARAY Polyol P-1010, and 0.04 g of dibutyl tin dilaurate were added. Then, while performing flushing with dry nitrogen, 13.0 g (58.3 mmol) of IPDI was added dropwise thereto while adjusting the dropwise addition rate such that the temperature is maintained at 80° C., and the reaction was allowed to occur for 4 hours at 80° C. Next, after cooling the reaction solution to 40° C., 0.2 g of MHQ was added thereto. Bubbling with dry air was carried out for 10 minutes. Then, 1.97 g (17.2 mmol) of "HEAA" was added. Under a dry air stream, stirring was continued for 5 hours while maintaining the temperature in the system at 60° C. As a result, 80.60 g of UT-15 was obtained as pale yellow liquid with viscosity. The yield was 96.3%. Similar to Synthesis Example 1, generation of a target urethane oligomer UT-15 was confirmed by an IR analysis. The number average molecular weight of the obtained urethane oligomer UT-15 was 10,800. The viscosity at 60° C. was found to be 36,000 mPa·s, and the low molecular weight component contained therein was 0.1%.

Synthesis Example 16

Synthesis of Urethane Oligomer UT-16

The same apparatus as that of Synthesis Example 1 was used. 50.0 g (50.0 mmol) of P-1010 (polyester polyol, manufactured by Kuraray Co., Ltd., number average molecular weight: 1000) was dissolved in 200 g of dehydrated acetone followed stirring for 30 minutes. Then, 11.1 g (16.7 mmol) of VESTANATT1890 (trimer of isophorone diisocyanate manufactured by Evonik Degussa) was added thereto. After increasing the temperature of the reaction solution to 65° C., 0.03 g of dibutyl tin dilaurate and 0.2 g of MHQ were added thereto and the reaction was allowed to occur at 3 hours. Then, 13.7 g (61.6 mmol) of IPDI was added thereto and the reaction was allowed to occur additionally for 3 hours. After that, 6.87 g (51.5 mmol) of "HEAA" was added thereto. Under a dry air stream, stirring was continued for 3 hours while maintaining the temperature in the system at 65° C. After that, the acetone was removed by a drying process under reduced pressure, and as a result, 65.0 g of UT-16 was obtained as transparent liquid with viscosity. The yield was 95.7%. Similar to Synthesis Example 1, generation of a urethane oligomer was confirmed by an IR analysis. When the low molecular weight component contained therein was measured, the result was found to be 8.0%. Thus, an additional purification step was carried out. The obtained urethane oligomer was subjected to re-precipitation by using a mixture liquid of MEK and water to remove the low molecular weight component. Under the reduced pressure, MEK and water were completely removed, and a target urethane oligomer UT-16 was obtained as pale yellow liquid with viscosity. The evaluation was carried out according to the method described above. The weight average molecular weight of the obtained UT-16 was 5,200. The viscosity at 60° C. was found to be 8,000 mPa·s, and the low molecular weight component contained therein was 0.9%.

Comparative Synthesis Example 1

Synthesis of Urethane Oligomer (UA-1)

The non-purified urethane oligomer obtained in Synthesis Example 16 (containing 8.0% of low molecular weight component) is referred to as UA-1. Furthermore, the evaluation was carried out according to the method described above. The weight average molecular weight of UA-1 was 5,000, and the viscosity at 60° C. was found to be 9,000 mPa·s.

Comparative Synthesis Example 2

Synthesis of Urethane Oligomer (UA-2)

The same apparatus as that of Synthesis Example 1 was used. 50.0 g (50.0 mmol) of P-1010 was dissolved in 200 g of dehydrated acetone followed stirring for 30 minutes. Then, 11.1 g (16.7 mmol) of Coronate HX (polyisocyanate manufactured by Tosoh Corporation) was added thereto and the temperature of the reaction solution was raised to 65° C. After that, 0.03 g of dibutyl tin dilaurate and 0.2 g of MHQ were added thereto and the reaction was allowed to occur at 3 hours. Then, 8.81 g (50.6 mmol) of TDI was added thereto and the reaction was allowed to occur additionally for 3 hours. After that, 4.31 g (37.2 mmol) of hydroxyethylacrylate (HEA) were added thereto. Under a dry air stream, stirring was continued for 3 hours while maintaining the temperature in the system at 65° C. After that, the acetone was removed by a drying process under reduced pressure, and as a result, 60.40 g of UA-2 was obtained as transparent liquid with viscosity. The yield was 95.9%. Similar to Synthesis Example 1, generation of a target urethane oligomer UA-2 was confirmed by an IR analysis. The number average molecular weight of the obtained urethane oligomer UA-2 was 4,900. The viscosity at 60° C. was found to be 6,000 mPa·s, and the low molecular weight component contained therein was 0.3%.

Comparative Synthesis Example 3

Synthesis of Urethane Oligomer (UA-3)

The same apparatus as that of Synthesis Example 1 was used. 50.0 g (50.0 mmol) of P-2012 (polyester polyol, manufactured by Kuraray Co., Ltd., number average molecular weight: 2000) and 0.04 g of dibutyl tin dilaurate were added. Then, while performing flushing with dry nitrogen, 12.0 g (54.1 mmol) of IPDI was added dropwise thereto while adjusting the dropwise addition rate such that the temperature is maintained at 80° C., and the reaction was allowed to occur for 6 hours at 80° C. Next, after cooling the reaction solution to 40° C., 0.2 g of MHQ was added thereto. Bubbling with dry air was carried out for 10 minutes. Then, 2.17 g (18.74 mmol) of HEA was added. Under a dry air stream, stirring was continued for 8 hours while maintaining the temperature in the system at 60° C. As a result, 113.7 g of pale yellow liquid with viscosity was obtained. The yield was 97.9%. Similar to Synthesis Example 1, generation of a urethane oligomer was confirmed by an IR analysis. The number average molecular weight of the obtained urethane oligomer UA-3 was 57,000. The viscosity at 60° C. was found to be 450,000 mPa·s, and the low molecular weight component contained therein was 0.8%.

Comparative Synthesis Example 4

Synthesis of Urethane Oligomer (UA-4)

The same apparatus as that of Synthesis Example 1 was used. 6.7 g (50.0 mmol) of dipropylene glycol (manufactured by Nacalai Tesque Inc., number average molecular weight: 134) and 15.0 g (50.0 mmol) of EDP-300 (polyether polyol, manufactured by ADEKA Corporation, number average molecular weight: 300) were dissolved in 100 g of dehydrated acetone followed stirring for 30 minutes. Then, 19.1 g (110.0 mmol) of toluene diisocyanate (TDI) was added thereto and stirring was continued for additional 30 minutes. Under a dry air stream, temperature of the reaction solution was raised to 65° C., and after adding 0.02 g of dibutyl tin dilaurate and 0.2 g of MHQ, the reaction was allowed to occur for 2 hours. Then, 25.2 g (217.0 mmol) HEA was added, and under a dry air stream, stirring was continued for 3 hours while maintaining the temperature in the system at 60° C. After that, the acetone was removed by a drying process under reduced pressure, and as a result, 47.1 g of UA-4 was obtained as transparent liquid with viscosity. The yield was 96.5%. Similar to Synthesis Example 1, generation of a target urethane oligomer UA-4 was confirmed by an IR analysis. The number average molecular weight of the obtained urethane oligomer UA-4 was 2,700. The viscosity at 60° C. was found to be 20,000 mPa·s, and the low molecular weight component contained therein was 8.2%.

The characteristics of the urethane oligomers obtained in Synthesis Examples 1 to 16 and Comparative Synthesis Examples 1 to 4 were evaluated according to the methods that are described below, and the results are described in Table 1. Furthermore, the solvent and monomer that are used for the evaluations are as follows.

IPA: isopropanol
MEK: methyl ethyl ketone
THF: tetrahydrofuran
"ACMO": N-acryloylmorpholine (manufactured by KJ Chemicals Corporation)
HDDA: 1,6-hexane diol diacrylate
BA: butyl acrylate
IBOA: isobornyl acrylate
2EHA: 2-ethylhexyl acrylate
THFA: tetrahydrofurfuryl acrylate
IBOA: isobornyl acrylate (4) Compatibility A general purpose solvent as a diluent and an acrylic monomer were added in an amount of 1 part by weight to 1 part by weight of the obtained urethane oligomer and stirred, then, the resulting product was allowed to stand overnight, and the extent of dissolution was examined by naked eye observation.

⊙: transparency was high, and cloudiness or separation was not observed at all.
○: although transparency was high, slight cloudiness was observed.
Δ: although layer separation did not occur, cloudiness was observed.
×: cloudiness was observed, and layer separation occurred.

As shown in the results of Table 1, it was found that, if the low molecular weight component like urethane adduct is included in an amount of more than 5% by weight in the (meth)acrylamide based urethane oligomer, it was found that the compatibility with a general purpose solvent and a monomer is significantly deteriorated, and it is difficult to be widely used in optical members or the like.

Using the urethane oligomers obtained in the Synthesis Examples and the Comparative Synthesis Examples, active energy ray curable resin compositions were prepared. Then, using these resin compositions, ultraviolet ray cured films were produced, and the characterization evaluation of the cured films was performed. The results are shown in Table 2.

Example A-1

100 parts by weight of the (meth)acrylamide based urethane oligomer UT-1 obtained in Synthesis Example 1, 100 parts by weight of methyl ethyl ketone (MEK), and 3 parts by weight of Irgacure 1173 as a photopolymerization initiator were homogeneously mixed, and thus an active energy ray curable resin composition was prepared. Thereafter, using the obtained curable resin composition, an ultraviolet ray cured film was produced by the following method.

Method for Producing Ultraviolet Ray Cured Film

By applying to the anchor coat surface of a polyethylene terephthalate (PET) film ("Cosmoshine A4100" manufactured by Toyobo Co., Ltd., one side was anchor-coat-treated) having a thickness of 100 μm using a bar coater (RDS 12), a coating film was prepared such that the thickness of the dried coating film became 10 μm. The obtained coating film was dried at 80° C. for 2 minutes in an explosion-proof dryer, and cured by irradiation (apparatus: inverter type conveyor system ECS-4011GX manufactured by Eye Graphics Co., Ltd., metal halide lamp: M04-L41 manufactured by Eye Graphics Co., Ltd.) with ultraviolet rays, and thus a ultraviolet ray cured film was prepared. The curing property of the resin composition, and tack resistance, shrinkage resistance (cure shrinkage rate), transparency, water absorption ratio, adhesion property, strength, and elongation of the obtained cured film were evaluated by the following methods. The results are shown in Table 2.

(5) Curing Property

A dried coating film with thickness of 10 μm was prepared as described in the above. Ultraviolet ray irradiation was carried out for 120 seconds at illumination intensity of 2 mW/cm$^2$ (cumulative amount of light: 240 mJ/cm$^2$). The height of a peak derived from a vinyl group of the resin composition (1630 cm$^{-1}$) was measured by real time FT-IR. Accordingly, the curing rate of a coating film was calculated (Curing rate (%)=(Height of peak derived from vinyl group before curing−Height of peak derived from vinyl group after curing)/(Height of peak derived from vinyl group before curing×100).

⊙: curing rate of 90% or more
○: curing rate of 80% or more but less than 90%
Δ: curing rate of 50% or more but less than 80%
×: curing rate of less than 50%

(6) Tack Resistance

A dried coating film with thickness of 10 μm was prepared as described in the above. Ultraviolet ray irradiation was carried out for 3 seconds at illumination intensity of 700 mW/cm$^2$ (cumulative amount of light: 2100 mJ/cm$^2$). Accordingly, a completely cured coating film (completely cured film) was prepared. By touching the surface of a completely cured film with a finger, stickiness state was evaluated.

⊙: there was no stickiness at all.
○: although there was slight stickiness, a finger mark did not remain on the surface.

Δ: there was stickiness, and a finger mark remained on the surface.
×: stickiness was severe, and a finger stuck to the surface.

(7) Shrinkage Resistance (Cure Shrinkage Rate)

With regard to the cure shrinkage rate, CUSTRON EU201C (manufactured by Acro Edge Co., Ltd.), which is a resin curing shrinkage stress measuring device, was used, and the measurement was carried out by using a laser extensometer. The cure shrinkage rate was calculated according to the method described in JP 2013-104869 A.

⊙: shrinkage resistance of less than 2.0%
○: shrinkage resistance of 2.0% or more but less than 4.0%
Δ: shrinkage resistance of 4.0% or more but less than 5.0%
×: shrinkage resistance of 5.0% or more (8) Transparency (Naked Eye Observation)

The completely cured coating film obtained in the above (6) was used and observed with a naked eye so that the transparency was evaluated.

⊙: it was transparent, and there was no opaqueness.
○: it was transparent, and there was slight opaqueness.
Δ: although there was opaqueness, transparent portions also remained.
×: there was severe opaqueness, and a transparent portion could not be confirmed.

(9) Water Absorption Ratio

A curable resin composition was poured on a Teflon resin sheet which was hollowed such that the depth became 1 mm. After vacuum-drying (50° C., 400 torr), curing was performed by ultraviolet ray irradiation (700 mW/cm$^2$, 2,000 mJ/cm$^2$). Accordingly, an ultraviolet ray cured sheet was produced. The obtained sheet was cut into 3 cm square to obtain a test piece. The obtained test piece was allowed to stand in an environment of a temperature of 50° C. and a relative humidity of 95% for 24 hours, and then the water absorption ratio was calculated according to Equation 1.

Water absorption ratio(%)=(Weight after incubation at thermostatic and humidistatic conditions−Weight before incubation at thermostatic and humidistatic conditions)/Weight before incubation at thermostatic and humidistatic conditions×100 [Equation 1]

(10) Adhesion Property

The completely cured obtained in the above (6) was used. Based on JIS K 5600, one hundred of squares of 1 mm×1 mm were created, and a cellophane tape was attached thereto. The evaluation was made by counting the number of squares in which the coating film remained on the substrate side when the tape was peeled all at once.

(11) Strength at Break·Elongation at Break

Measurement was performed by using the completely cured coating film obtained in the above (6) in an environment of a temperature of 25° C. and a relative humidity of 50% according to JIS K 7127.

Measurement device: Tensilon Universal Tester RTA-100 (manufactured by Orientec Co., Ltd.)
Test conditions: test speed of 10 mm/min
Test piece size: gauge length of 25 mm, width of 15 mm, thickness of 50 μm.

Examples A-2 to 16 and Comparative Examples A-17 to 20

In the same manner as in Example A-1 except that the compositions described in Table 2 were used, an ultraviolet ray curable resin composition was prepared, a cured film was produced, and evaluation was carried out by the above method. The results are shown in Table 2.

As shown in the results of the Evaluation Examples and the Comparative Evaluation Examples, a cured product obtained from the (meth)acrylamide based urethane oligomer in which a low molecular weight component compound like urethane adduct is contained in an amount of more than 5% by weight exhibits poor shrinkage resistance, water absorption ratio, and transparency. It is believed to be due to the reason that a low molecular weight component is a component with high polarity. Namely, it is believed by the inventors of the present invention that, as a low molecular weight component is contained, overall polarity of the urethane oligomer is increased and the water absorption ratio is lowered. Furthermore, solubility of a low molecular weight component is deteriorated and the obtained cured film has poor transparency and shrinkage rate. Furthermore, although the cure shrinkage rate of less than 5% is achieved by the polyfunctional (meth)acrylamide based urethane oligomer, in the case of a polyfunctional (meth)acrylate based urethane oligomer, the cure shrinkage rate is 5% or more, showing poorer shrinkage resistance. This is believed to be a result of dense alignment of molecules due to an aggregation force between acrylamide groups (hydrogen bond formed between amide groups and between amide group and urethane group) and less shrinkage caused by curing. Furthermore, even when the low molecular weight component is not contained at more than 5% by weight, it was unable to obtain the satisfying curing property and tack resistance that can be obtained with the (meth)acrylamide.

The (meth)acrylamide based urethane oligomer of the present invention has sufficiently satisfying shrinkage resistance, and the curable resin composition has an excellent curing property, tack resistance, transparency, and water resistance, as well as improved adhesion property on PET non-treated surface and PMMA.

The characteristics evaluation in each field of application was performed by using the urethane oligomers obtained in Synthesis Examples 1 to 16 and Comparative Synthesis Examples 1 to 4. The materials used in Examples and the Comparative examples are as follows.

"HEAA": hydroxyethyl acrylamide (manufactured by KJ Chemicals Corporation)
"DMAA": N,N-dimethyl acrylamide (manufactured by KJ Chemicals Corporation)
"DEAA": N,N-diethyl acrylamide (manufactured by KJ Chemicals Corporation)
"ACMO": N-acryloylmorpholine (manufactured by KJ Chemicals Corporation)
"DMAPAA": dimethylaminopropyl acrylamide (manufactured by KJ Chemicals Corporation)
HEA: hydroxyethyl acrylate
2EHA: 2-ethylhexyl acrylate
EEA: 2-(2-ethoxyethoxy)ethyl acrylate
THFA: tetrahydrofurfuryl acrylate
IBOA: isobornyl acrylate
CHA: cyclohexyl acrylate
HDDA: 1,6-hexane diol diacrylate
TPGDA: tripropylene glycol diacrylate
PETA: pentaerythritol triacrylate
DPHA: dipentaerythritol hexaacrylate
4HBA: 4-hydroxybutyl acrylate
TMPTA: trimethylol propane triacrylate
DMAEA-TFSIQ: acryloyloxyethyltrimethylammonium bis(trifluoromethanesulfonyl)imide (manufactured by KJ Chemicals Corporation)
DMAPAA-TFSIQ: acryloylaminopropyltrimethylammonium bis(trifluoromethanesulfonyl)imide (manufactured by KJ Chemicals Corporation)
UV7600B: ultraviolet ray curing type urethane acrylate resin (Nippon Gohsei)
A-LEN-10: ethoxyated-o-phenylphenol acrylate (manufactured by Shin Nakamura Chemical Co., Ltd.)
CHMA: cyclohexyl methacrylate
Light acrylate PE-4A: pentaerythritol tetraacrylate
Silica microparticles: product name IPA-ST-L (manufactured by Nissan Chemical Industries, Ltd.) solid content of 30%
IBMA: N-isobutoxymethyl acrylamide
Irgacure 184: 1-hydroxy-cyclohexyl-phenyl-ketone (manufactured by BASF Japan Ltd.)
8019add: silicone based surface modifying agent manufactured by Dow Corning Toray
Irgacure 1173: 2-hydroxy-2-methyl-1-phenyl-propan-1-one (manufactured by BASF Japan Ltd.)
UV3700B: urethane acrylate resin (manufactured by Nippon Gohsei)
UV4200B: urethane acrylate resin (manufactured by Nippon Gohsei)
Irgacure TPO: 2,4,6-trimethylbenzoyl-diphenyl-phosphine oxide (manufactured by BASF Japan Ltd.)

Evaluation Example B-1

25 parts by weight of the (meth)acrylamide based urethane oligomer UT-1 synthesized in Synthesis Example 1, 10 parts by weight of "HEAA", 40 parts by weight of 2EHA, 9 parts by weight of CHA, 15 parts by weight of EEA, and 1 part by weight of DMAEA-TFSIQ as an ionic vinyl monomer were admixed with one another. Then, 3 parts by weight of Irgacure 184 as a photopolymerization initiator were added thereto, and the resulting product was homogeneously mixed, and thus an ultraviolet ray curable cohesive was prepared. Thereafter, using the obtained cohesive, a cohesive sheet was produced by ultraviolet ray curing according to the following method, and evaluation thereof was performed.

Method for Producing Ultraviolet Ray Curing Type Cohesive Sheet

The ultraviolet ray curing type cohesive prepared in the above was applied to a heavy peeling separator (silicone coated PET film), then, using a desktop type roll laminator (RSL-382S manufactured by Royal Sovereign), a light peeling separator (silicone coated PET film) was attached thereto such that the thickness of the cohesive layer became 25 μm and air bubbles were not to be bitten, and irradiation (apparatus: inverter type conveyor system ECS-4011GX manufactured by Eye Graphics Co., Ltd., metal halide lamp: M04-L41 manufactured by Eye Graphics Co., Ltd., ultraviolet illumination intensity: 700 mW/cm$^2$, cumulative amount of light: 1000 mJ/cm$^2$) with ultraviolet rays was performed, and thus an optical transparent cohesive sheet was prepared. The characteristics of the obtained cohesive sheet were evaluated by the following methods. The results are shown in Table 3.

(12) Transparency (Transmittance)

Under conditions of a temperature of 23° C. and a relative humidity of 50%, the surface from which the light peeling separator had been peeled, of the cohesive sheet cut into a shape with a width of 25 mm was attached to a glass substrate as an adherend, then, a heavy peeling separator was peeled, and the transmittance was measured. After the total light transmittance of the glass substrate was measured using a haze meter (NDH-2000 manufactured by Nippon Denshoku Industries Co., Ltd.) according to JIS K 7105, by subtracting the transmittance of the glass plate, the transmittance of the cohesive layer itself was calculated, and the transparency was evaluated. As the transmittance was higher, the transparency was better.

(13) Measurement of Surface Resistivity

Using a template (height 110×width 110 mm), the cohesive sheet was cut with a cutter knife, and the cut cohesive sheets were put in a thermostatic and humidistatic apparatus adjusted to a temperature of 23° C. and a relative humidity of 50% and allowed to stand for 3 hours followed by additional peeling of the heavy peeling separator, and thus a sample for surface resistivity measurement was obtained. The surface resistivity was measured using a digital electrometer (R8252 type: manufactured by ADC CORPORATION) according to JIS K 6911.

(14) Cohesive Force

Under conditions of a temperature of 23° C. and a relative humidity of 50%, transfer to a polyethylene terephthalate (PET) film (thickness of 100 μm) or a glass substrate as an adherend was carried out. After that, by reciprocally moving two times a pressure roller of a load of 2 kg, pressure-attachment was performed, and the resulting product was allowed to stand for 30 minutes in the same environment. Thereafter, using a tension tester (apparatus name: Tensilon RTA-100 manufactured by ORIENTEC Co., Ltd.), the 180° peeling resistance (N/25 mm) was measured at a peeling rate of 300 mm/min.

⊙: 30 (N/25 mm) or higher.
◯: 15 (N/25 mm) or higher but lower than 30 (N/25 mm).
Δ: 8 (N/25 mm) or higher but lower than 15 (N/25 mm).
×: lower than 8 (N/25 mm)

(15) Contamination Resistance

A cohesive sheet was attached to an adherend in the same manner as in the measurement of cohesive force described above, then, the resulting product was allowed to stand at 80° C. for 24 hours, and contamination of the adherend surface after the cohesive sheet was peeled was observed with a naked eye.

⊙: there is no contamination.
◯: there is very slight contamination.
Δ: there is slight contamination.
×: there are glue (cohesive) residues.

(16) Yellowing Resistance

A cohesive sheet was attached to a glass substrate, then, the resultant was set to a xenon fade meter (SC-700-WA: manufactured by Suga Test Instruments Co., Ltd.), and after irradiation with ultraviolet rays was performed at an intensity of 70 mW/cm$^2$ for 120 hours, the color change of the cohesive sheet was observed with a naked eye.

⊙: yellowing cannot be observed with a naked eye at all.
◯: very slight yellowing can be observed with a naked eye.
Δ: yellowing can be observed with a naked eye.
×: obvious yellowing can be observed with a naked eye.

(17) Moisture and Heat Resistance

A cohesive sheet was attached to a glass substrate in the same manner as in the yellowing resistance test described above, and kept for 100 hours under conditions of a temperature of 85° C. and a relative humidity of 85%. After that, an occurrence of floating, peeling, bubbles, or cloudiness was observed with a naked eye, and based on that, evaluation was performed.

⊙: it is transparent, and floating/peeling and bubble do not occur.
◯: although there is very slight opaqueness, floating/peeling and bubble do not occur.
Δ: there are slight opaqueness or floating/peeling, and bubbles.
×: there are severe opaqueness or floating/peeling, and bubbles.

(18) Step Followability

A black tape having a thickness of 20 μm was attached to a glass substrate, and thus a stepped glass was produced. After a cohesive sheet was transferred to the stepped glass, by reciprocating once (pressing speed of 300 mm/min) using a roller of a load of 2 kg on the sheet surface in an environment of a temperature of 23° C. and a relative humidity of 50%, pressure-attachment was performed, then, the resulting product was allowed to stand at a temperature of 80° C. for 24 hours, and the state of the stepped portion was observed using an optical microscope.

⊙: bubbles are not observed at all.
◯: slightly small spherical bubbles are observed.
Δ: large bubbles are observed, and there is a case where bubbles are connected to each other.
×: large bubbles are connected to each other, and spread on the line in the stepped portion.

(19) Punching Processability

The obtained cohesive sheet was cut by a Thompson punching method (punching method by punching blades, in which 10 linear blades were arranged at 5.0 mm intervals in parallel).

⊙: nothing remains on the punching blades.
◯: slight cohesive remains on the punching blades.
Δ: cohesive remains on the punching blades.
×: cohesive significantly remains on the punching blades, and cutting surface cannot be clearly observed.

Evaluation Examples B-2 to 9 and Comparative Evaluation Examples B-10 to 13

An ultraviolet ray curable resin was prepared in the same manner as Evaluation Example B-1 except that the composition described in Table 3 is used instead. A cohesive sheet was also prepared. The evaluation was made based on the methods described above. The results are shown in Table 3.

As shown in the results of the Evaluation Examples and the Comparative Evaluation Examples, the (meth)acrylamide based urethane oligomer in which a low molecular weight component compound like urethane adduct is contained in an amount of more than 5% by weight tends to have deteriorated transparency, cohesive force, and moisture and heat resistance, and, from the viewpoint that a cohesive sheet after curing shows poor contamination resistance and punching processability, it is difficult to be used. Meanwhile, contamination resistance and punching processability of the (meth)acrylate based urethane oligomer were not favourable due to poor tack resistance, if the content of the low molecular weight component is 5% by weight or less.

Furthermore, an oligomer with number average molecular weight of less than 3500 tends to have generation of a large amount of an urethane adduct with general molecular weight of less than 500 as a by-product, and thus it has poor followability, moisture resistance, and adhesion property. However, with the (meth)acrylamide based urethane oligomer of the present invention, it is possible to obtain a cohesive sheet which has not only high transparency and cohesive force but also excellent contamination resistance and punching processability.

Evaluation Example B-14

40 parts by weight of (meth)acrylamide based urethane oligomer UT-1 synthesized in Synthesis Example 1, 15 parts by weight of "HEAA", 15 parts by weight of "DEAA", 30 parts by weight of 2EHA, 3 parts by weight of DMAPAA-TFSIQ as an ionic vinyl monomer, and 3 parts by weight of Irgacure 184 as a photopolymerization initiator were added and homogeneously mixed, and used for a cohesive layer of a laminate for touch panel. The laminate consists of 2 pieces of a transparent electrode sheet and a cover glass, and it is a capacitive touch panel sensor having two laminated pieces of an electrode sheet which has an electrode for position detection provided on a single surface of a transparent substrate. By laminating the cohesive assembled as above on an opening of a line part consisting of copper using a laminator and irradiating (apparatus: inverter type conveyor system ECS-4011GX manufactured by Eye Graphics Co., Ltd., metal halide lamp: M04-L41 manufactured by Eye Graphics Co., Ltd., ultraviolet illumination intensity: 700 mW/cm$^2$, cumulative amount of light: 1000 mJ/cm$^2$) with ultraviolet ray, a cohesive agent layer was formed.

(20) Transparency (Transmittance)

Evaluation was made with the same test method as above 0080.

(21) Cohesive Force

Evaluation was made with the same test method as above 0080.

(22) Yellowing Resistance

Evaluation was made with the same test method as above 0080.

(23) Presence or Absence of Air Bubbles

For the cohesive agent layer which is formed on an opening of an electrode sheet to form a cohesive agent layer on an electrode sheet, size and number of air bubbles were evaluated.

⊚: there are less than 10 air bubbles with diameter of less than 0.5 mm

○: there are 10 or more but less than 30 air bubbles with diameter of less than 0.5 mm Δ: there are 30 or more air bubbles with diameter of less than 0.5 mm ×: there is at least one air bubble with diameter of 0.5 mm or more

(24) Recognisability

A touch panel assembled by using an electrode sheet was adhered on a display screen of a liquid crystal display device, and, when white color is displayed by operating the liquid crystal display device, presence of any lines that can be visually recognized was confirmed with a naked eye.

⊚: no line can be confirmed with a naked eye at all.
○: very slight line can be confirmed with a naked eye at all.
Δ: line can be confirmed with a naked eye at all.
×: obvious line can be confirmed with a naked eye at all.

Evaluation Examples B-14 to 18 and Comparative Evaluation Examples B-19 and 20

A cohesive layer was prepared in the same manner as Evaluation Example B-14 except that the composition described in Table 3-2 is used instead. The evaluation was made based on the methods described above. The results are shown in Table 3-2.

As it can be recognized from Table 3-2, the cohesive used for a touch panel laminate of the present invention exhibited an excellent adhesion property on copper, and it was possible to obtain a cohesive agent which has high effect of suppressing air bubbles in cohesive layer during formation of a cohesive layer.

Evaluation Example C-1

25 parts by weight of (meth)acrylamide based urethane oligomer UT-1 synthesized in Synthesis Example 1, 15 parts by weight of "ACMO", 20 parts by weight of "DMAA", 25 parts by weight of HEA, and 15 parts by weight of THFA were mixed, and 3 parts by weight of Irgacure 1173 as a photopolymerization initiator were added. According to homogenous mixing, an ultraviolet ray curable adhesive was prepared. After that, by using the obtained adhesive, a polarizing plate was produced by ultraviolet curing and evaluation of physical properties of the polarizing plate was carried out according to the following methods.

Production of Polarizing Plate by UV Irradiation

Using a desktop type roll laminator (RSL-382S manufactured by Royal Sovereign), a polarizing film (polarizer) was sandwiched between two sheets of transparent films (one of a protective film, a phase difference film, or an optical compensation film can be used, and in the present invention, an acryl film was used as a protective film), and the adhesive of Example or Comparative example was applied between the transparent film and the polarizing film such that the thickness became 10 μm. By performing irradiation (apparatus: inverter type conveyor system ECS-4011GX manufactured by Eye Graphics Co., Ltd., metal halide lamp: M04-L41 manufactured by Eye Graphics Co., Ltd., ultraviolet illumination intensity: 700 mW/cm$^2$, cumulative amount of light: 1000 mJ/cm$^2$) with ultraviolet rays from the upper surface of the attached transparent film, a polarizing plate having a transparent film on both sides of the polarizing film was produced.

(25) Observation of Surface Shape

The surface of the obtained polarizing plate was observed with a naked eye, and evaluation was performed according to the following criteria.

⊚: fine lines and irregularity cannot be observed on the surface of the polarizing plate.
○: fine lines can be partly observed on the surface of the polarizing plate.
Δ: fine lines and irregularity can be observed on the surface of the polarizing plate.
×: obvious lines and irregularity can be observed on the surface of the polarizing plate.

(26) Peeling Strength

Under conditions of a temperature of 23° C. and a relative humidity of 50%, a polarizing plate (test piece) cut into 20 mm×150 mm was attached to a test plate attached to a tension tester (Autograph AGXS-X 500N manufactured by Shimadzu Corporation) using a double-sided adhesive tape. A transparent protective film on the side which was not attached with a double-sided adhesive tape, and one piece of the polarizing film were peeled at about 20 to 30 mm in advance and chucked to an upper clamping tool, and the 90° peeling strength (N/20 mm) was measured at a peeling rate of 300 mm/min.

⊚: 3.0 (N/20 mm) or greater.
○: 1.5 (N/20 mm) or greater but less than 3.0 (N/20 mm).
Δ: 1.0 (N/20 mm) or greater but less than 1.5 (N/20 mm).
×: less than 1.0 (N/20 mm).

(27) Water Resistance

The obtained polarizing plate was cut into 20×80 mm, then, it was soaked in warm water at 60° C. for 48 hours, and the presence or absence of peeling at the interfaces between the polarizer and the protective film, the phase difference film, and the optical compensation film was observed. Determination was performed according to the following criteria.

⊚: there is no peeling at the interface between the polarizer and the protective film (less than 1 mm).

○: there is peeling at a part of the interface between the polarizer and the protective film (1 mm or greater but less than 3 mm).

Δ: there is peeling at a part of the interface between the polarizer and the protective film (3 mm or greater but less than 5 mm).

×: there is peeling at the interface between the polarizer and the protective film (5 mm or greater).

(28) Durability

After the obtained polarizing plate was cut into 150 mm×150 mm, the cut polarizing plate was put into a thermal shock apparatus (TSA-101L-A manufactured by ESPEC CORP.), then, heat shock at −40° C. to 80° C. was performed 100 times for 30 minutes, respectively, and evaluation was carried out according to the following criteria.

⊙: cracks do not occur.

○: short cracks of 5 mm or smaller occur only at the ends.

Δ: cracks occur in a short linear shape at places other than the ends, but the polarizing plate is not separated into two or more portions by that line.

×: cracks occur at places other than the ends, and by the line, the polarizing plate is separated into two or more portions.

Evaluation Examples C-2 to 9 and Comparative Evaluation Examples C-10 to 13

An ultraviolet ray curable resin was prepared in the same manner as Evaluation Example C-1 except that the composition described in Table 4 is used instead. The evaluation was made based on the methods described above. The results are shown in Table 4.

As shown in the results of the Evaluation Examples and the Comparative Evaluation Examples, with the (meth) acrylamide based urethane oligomer in which the molecular weight and acryl equivalents are outside the suitable range, urethane modified (meth)acrylate, (meth)acrylamide based urethane oligomer in which a low molecular weight component is contained at more than 5% by weight, and (meth) acrylate based urethane oligomer in which a low molecular weight component is contained at 5% by weight or less, the peeling strength was low and the water resistance and durability of the obtained polarizing plate were insufficient, and it is believed to be caused by floating of a cured film as a result of insufficient shrinkage resistance. Furthermore, when the urethane modified (meth)acrylate with high viscosity is used, lines are shown on a surface of a polarizing plate and there was a problem in terms of the surface shape, and thus it cannot be used for desired use. However, the polarizing plate obtained by using the (meth)acrylamide based urethane oligomer of the present invention showed no lines or irregular unevenness on surface. Furthermore, it was possible to obtain an adhesive composition for polarizing plate which has high peeling strength while having water resistance and durability.

Evaluation Example D-1

23 parts by weight of (meth)acrylamide based urethane oligomer UT-1 synthesized in Synthesis Example 1, 16 parts by weight of UV-7600, 20 parts by weight of PETA, 12 parts by weight of DPHA, 17 parts by weight of "ACMO", and 12 parts by weight of THFA were mixed, and 3 parts by weight of Irgacure 1173 as a photopolymerization initiator were added. According to homogenous mixing, a photocurable coating composition was prepared.

(29) Compatibility

The compatibility of the coating agent composition obtained by the above method was observed with a naked eye.

⊙: transparency of the coating composition is high, and cloudiness or separation is not observed at all.

○: although transparency of the coating composition is high, slight cloudiness is observed.

Δ: cloudiness is observed over the entire coating composition.

×: cloudiness of the coating composition is observed, and separation occurs.

(30) Wettability

The obtained coating agent composition was applied to a substrate, and the adhered state of the coating film was observed with a naked eye.

⊙: even immediately after applying, or after being allowed to stand for 5 minutes, a smooth coating film was formed with no floating.

○: there was no floating immediately after application, but after being allowed to stand for 5 minutes, slight floating was observed.

Δ: slight floating was observed immediately after application.

×: significant floating was observed immediately after application, and a uniform coating film was not obtained.

Production of Coating Film by Ultraviolet Ray Irradiation

The obtained coating agent composition was applied to a PET film having a thickness of 100 μm using a bar coater (RDS 12). By performing irradiation (apparatus: inverter type conveyor system ECS-4011GX manufactured by Eye Graphics Co., Ltd., metal halide lamp: M04-L41 manufactured by Eye Graphics Co., Ltd., ultraviolet illumination intensity: 700 mW/cm², cumulative amount of light: 1000 mJ/cm²) with ultraviolet rays, a coating film was produced, and evaluation was carried out by the following method. The results are shown in Table 6. In a case where a solvent was used, ultraviolet ray irradiation was performed after drying at 80° C. for 3 minutes after coating.

(31) Curing Property

The coating agent composition was applied, then, the obtained coating film was irradiated with ultraviolet rays with ultraviolet illumination intensity of 700 mW/cm², and the cumulative amount of light till to have complete curing of the resin composition was measured. The complete cure means a state in which, when the surface of the cured film is rubbed with silicone rubber, no trace is present.

⊙: completely cured at a cumulative amount of light of 1000 mJ/cm².

○: completely cured at a cumulative amount of light of 1000 mJ/cm² to 2,000 mJ/cm².

Δ: completely cured at a cumulative amount of light of 2,000 mJ/cm² to 5,000 mJ/cm².

×: a cumulative amount of light of 5,000 mJ/cm² or greater is required until completely cures.

(32) Tack Resistance

The surface of the coating film obtained by the above method was touched with a finger, and the degree of stickiness was evaluated.

⊙: there is no stickiness.

○: although there is slight stickiness, a finger mark does not remain on the surface.

Δ: there is stickiness, and a finger mark remains on the surface.

×: stickiness is strong, and a finger sticks to the surface.

(33) Shrinkage Resistance (Curl Resistance)

A coating film obtained by irradiating the coating film obtained by the above method with ultraviolet rays (ultraviolet illumination intensity of 700 mW/cm$^2$, cumulative amount of light of 2,000 mJ/cm$^2$) was cut into 10 cm square, and the average of floating of the four corners was measured.
⊙: floating of 0.5 mm or less was found.
◯: floating of 1 mm or less was found.
Δ: floating of 3 mm or less was found.
×: huge curl was found.
(34) Scratch Resistance Steel wool of #0000 was reciprocally moved ten times while a load of 200 g/cm$^2$ was applied, and the presence of an occurrence of scratches was evaluated with a naked eye.
⊙: peeling of a film and occurrence of scratches are hardly observed.
◯: fine scratches are slightly observed on a part of a film.
Δ: streaky scratches are observed on the entire film surface.
×: peeling of a film occurs.
(35) Adhesion Property According to JIS K 5600, one hundred of squares of 1 mm×1 mm were created, then, a cellophane tape was attached thereto, and evaluation was performed by counting the number of squares in which the coating film remained on the substrate side when the tape was peeled all at once.
(36) Moisture Resistance The coating film obtained on a PET film (100 μm) was allowed to stand in an environment of a temperature of 50° C. and a relative humidity of 95% for 24 hours, and the subsequent film was evaluated with a naked eye or by an adhesion property test.
⊙: transparency is maintained at high temperature and high humidity, and deterioration of adhesion property is not observed.
◯: although transparency is maintained at high temperature and high humidity, slight deterioration of adhesion property is observed.
Δ: although transparency is maintained at high temperature and high humidity, significant deterioration of adhesion property is observed.
×: deterioration of transparency at high temperature and high humidity or deterioration of adhesion property is observed.
(37) Self Restoring Property The coating film obtained by the above method was scratched using a spoon and allowed to stand in an environment of a temperature of 25° C. and a relative humidity of 50%, and the recovery state from scratches was evaluated with a naked eye.
⊙: scratches are completely recovered within 30 minutes.
◯: scratches are completely recovered within 30 minutes to 5 hours.
Δ: scratches are completely recovered within 5 hours to 24 hours.
×: scratches are not completely recovered even after being allowed to stand for 24 hours.

Evaluation Examples D-2 to 8 and Comparative Evaluation Examples D-10 to 13

A coating composition was prepared in the same manner as Evaluation Example D-1 except that the composition described in Table 5 is used instead. A cured film was also prepared based on the methods described above. The evaluation was made based on the methods described above. The results are shown in Table 5.

Evaluation Examples D-14 to 17 and Comparative Evaluation Examples D-18 and 19

A self restoring coating composition was prepared in the same manner as Evaluation Example D-1 except that the composition described in Table 6 is used instead. A cured film was also prepared based on the methods described above. The evaluation was made based on the methods described above. The results are shown in Table 6.

As shown in the results of the Evaluation Examples and the Comparative Evaluation Examples, the urethane modified (meth)acrylate or the urethane modified (meth)acrylamide which has molecular weight, acryl equivalents, and viscosity that are outside a certain range were not satisfactory in terms of the curing shrinkage resistance, water resistance, adhesion property, and curing. In particular, with regard to the oligomer containing a large amount of a urethane adduct with number average molecular weight of less than 1000 and the acrylate oligomer, the obtained cured product exhibited poor compatibility and a decrease in transparency, adhesion property, and water resistance of a cured film. On the other hand, as the urethane oligomer of the present invention is a (meth)acrylamide based oligomer and contains a low molecular weight component in an amount of 5% by weight or less, a coating agent composition which has an excellent curing property and exhibits favourable results in terms of the moisture resistance, adhesion property, and tack resistance can be obtained, and thus it can be suitably used for applications like a decorative film, a self restoring coating agent, or hard coating.

Evaluation Example E-1

42 parts by weight of (meth)acrylamide based urethane oligomer UT-1 synthesized in Synthesis Example 1, 20 parts by weight of "HEAA", 10 parts by weight of "DEAA", 15 parts by weight of 4-HBA, and 13 parts by weight of A-LEN-10 were mixed, and 3 parts by weight of Irgacure 1173 as a photopolymerization initiator were added. According to homogenous mixing, an ultraviolet ray curable sealing agent was prepared. After that, by using the obtained sealing agent, a cured product of a sealing agent resin produced by ultraviolet curing and evaluation of physical properties were carried out according to the following methods.
Method for Producing Cured Product of Ultraviolet Ray Curing Type Sealing Agent Resin A silicon spacer (height 30 mm×width 15 mm×thickness 3 mm) was set on a glass plate (height 50 mm×width 50 mm×thickness 5 mm), and the ultraviolet ray curing type sealing agent prepared above was injected to the inside of the spacer. After thorough deaeration, by performing irradiation with ultraviolet rays (apparatus: inverter type conveyor system ECS-4011GX manufactured by Eye Graphics Co., Ltd., metal halide lamp: M04-L41 manufactured by Eye Graphics Co., Ltd., ultraviolet illumination intensity: 700 mW/cm$^2$, cumulative amount of light: 1000 mJ/cm$^2$), a cured product of a sealing agent resin was produced. The characteristics of the obtained cured product were evaluated by the following methods. The results are shown in Table 6.
(38) Transparency (Transmittance)

The obtained cured product was allowed to stand in an environment of a temperature of 23° C. and a relative humidity of 50% for 24 hours. Thereafter, the transmittance of the cured film was measured using a haze meter (NDH-2000 manufactured by Nippon Denshoku Industries Co., Ltd.), and the transparency was evaluated on a scale of four levels that are described below.
⊙: transmittance is 90% or greater.
◯: transmittance is 85% or greater but less than 90%.
Δ: transmittance is 50% or greater but less than 85%.
×: transmittance is less than 50%.

(39) Light Resistance

The obtained cured product was attached to a glass substrate, and the degree of yellowing was measured by using a spectrophotometer (CM-3600d manufactured by Konica Minolta, Inc.). Thereafter, the cured product was set to a xenon fade meter (SC-700-WA manufactured by Suga Test Instruments Co., Ltd.), and after irradiation with ultraviolet rays was performed at an intensity of 4 W/cm$^2$ at 30° C. for 100 hours, the degree of yellowing after the irradiation was measured in the same manner as before the irradiation, and the color change of the cured product was observed with a naked eye.

⊙: yellowing cannot be observed at all with a naked eye.
○: very slight yellowing can be observed with a naked eye.
Δ: yellowing can be observed with a naked eye.
×: obvious yellowing can be observed with a naked eye.

(40) Water Absorption Ratio Test 1 g of a test specimen was taken from the obtained cured product, set in a thermostatic and humidistatic apparatus of a temperature 85° C. and a relative humidity of 95%, and allowed to stand for 48 hours, then, the test piece was weighed again, and the water absorption ratio was calculated in the same manner as the above evaluation item (9).

⊙: water absorption ratio is less than 1.0%
○: water absorption ratio is 1.0% or greater but less than 2.0%
Δ: water absorption ratio is 2.0% or greater but less than 3.0%
×: water absorption ratio is 3.0% or greater

(41) Out Gas Test 1 g of a test specimen was taken from the obtained cured product. The test specimen was then allowed to stand in a thermostat set to a temperature of 100° C., dry nitrogen was flowed thereto for 24 hours, then, the test piece was weighed again, and the outgas generation rate was calculated according to (Equation 2).

Out gas generation rate (%)=(Weight after incubation at thermostatic conditions−Weight before incubation at thermostatic conditions)/Weight before incubation at thermostatic conditions× 100      (Equation 2)

⊙: generation rate is less than 0.1%
○: generation rate is 0.1% or greater but less than 0.3%
Δ: generation rate is 0.3% or greater but less than 1.0%
×: generation rate is 1.0% or greater

(42) Heat Cycle Resistance

One cycle in which the obtained cured product was allowed to stand at −40° C. for 30 minutes, and then at 100° C. for 30 minutes was repeated 10 times, and the state of the cured product was observed with a naked eye.

⊙: change is not observed at all.
○: although bubbles slightly occur, occurrence of cracks is not observed, and it is transparent.
Δ: occurrence of some of bubbles or cracks is observed, and there is slight opaqueness.
×: bubbles or cracks fully occur, and it is a semi-transparent state.

Evaluation Examples E-2 to 8 and Comparative Evaluation Examples E-9 to 12

An ultraviolet ray curable sealing agent was prepared in the same manner as Evaluation Example E-1 except that the composition described in Table 7 is used instead. The evaluation was made based on the methods described above. The results are shown in Table 7.

As shown in the results of Evaluation Examples and Comparative Evaluation Examples, in a case where a urethane oligomer including 5% by weight or more of a component having a molecular weight less than 1000 was blended, the transparency and light resistance of the obtained cured product were decreased, and the water absorption ratio was also high. Furthermore, from the urethane modified (meth)acrylate and the urethane modified (meth)acrylamide which has molecular weight, acryl equivalents, and viscosity that are outside a certain range, decreased water resistance caused by curing shrinkage and generation of out gas were exhibited. On the other hand, in a case where the comparative examples of the present invention are used, an excellent property was shown in terms of all of the required characteristics, and it can be widely used as a sealing agent for electronic parts, semiconductors, solar cells, or the like.

Evaluation Example F-1

9 parts by weight of (meth)acrylamide based urethane oligomer UT-1 synthesized in Synthesis Example 1, 35 parts by weight of HDDA, 30 parts by weight of THFA, 20 parts by weight of IBOA, 3 parts by weight of a pigment, and 3 parts by weight of pigment dispersant were mixed, and 5 parts by weight of Irgacure TPO as a photopolymerization initiator were added. According to homogenous mixing, a photocurable ink composition was prepared. After that, inkjet printing and evaluation of the obtained printed matter were carried out according to the following methods.

(43) Viscosity

The viscosity of the obtained ink composition was measured by using a cone-plate type viscometer (apparatus name: RE550 viscometer manufactured by Toki Sangyo Co., Ltd.) according to JIS K5600-2-3. Based on ink jet type printing, the viscosity of the ink composition at 20° C. is preferably 3 to 20 mPa·s, and more preferably 5 to 18 mPa·s. If the viscosity is less than 3 mPa·s, print smearing after discharge and reduction of discharge followability by printing deviation are seen, and if the viscosity is 20 mPa·s or greater, reduction of discharge stability due to clogging of discharge nozzles is seen, and thus not desirable.

(44) Compatibility

The compatibility of the ink composition prepared by the above method was observed with a naked eye.

⊙: an insoluble material is not observed in the ink composition.
○: slight insoluble materials are observed in the ink composition.
Δ: insoluble materials are observed over the entire ink composition.
×: precipitates are observed in the ink composition.

Production of Printed Matter by UV Irradiation

The obtained ink composition was applied using a bar coater (RDS 12) onto a polyethylene terephthalate (PET) film having a thickness of 100 μm. According to curing by ultraviolet ray irradiation (apparatus: inverter type conveyor system ECS-4011GX manufactured by Eye Graphics Co., Ltd., metal halide lamp: M04-L41 manufactured by Eye Graphics Co., Ltd.), a printed matter was produced.

(45) Curing Property

When a printed matter was produced by the above method, the cumulative amount of light till to have complete curing of the ink composition was measured.

⊙: completely cured at 1000 mJ/cm$^2$
○: completely cured at 1000 to 2000 mJ/cm$^2$
Δ: completely cured at 2000 to 5000 mJ/cm$^2$ x: 5000 mJ/cm² or higher is required to have complete curing.

(46) Surface Dryness

After the printed matter which has been produced by the above method was allowed to stand in an environment of a temperature of 23° C. and a relative humidity of 50% for 5 minutes, high quality paper was superimposed on the printed surface, then, a load of 1 kg/cm² was applied thereto over a period of 1 minute, and the degree of transfer of ink to the paper was evaluated.

⊙: ink was dried, and transfer to the paper did not occur at all.
○: ink was dried, and slight transfer to the paper occurred.
Δ: ink was nearly dried, and transfer to the paper occurred.
x: ink was hardly dried, and significant transfer to the paper occurred.

Inkjet Printing and Printability Evaluation

A solid image was printed using an ink jet type color printer (PM-A890 manufactured by Seiko Epson Corporation), and by performing irradiation with ultraviolet rays (apparatus: inverter type conveyor system ECS-4011GX manufactured by Eye Graphics Co., Ltd., metal halide lamp: M04-L41 manufactured by Eye Graphics Co., Ltd., ultraviolet illumination intensity: 700 mW/cm², cumulative amount of light of 1,000 mJ/cm²), a printed matter was produced, and evaluation was carried out by the following method. The results are shown in Table 5.

(47) Discharge Stability

Printing was performed using the inkjet printer described above, and the print state of the printed matter was evaluated with a naked eye.

⊙: there was no nozzle absence, and it was well printed.
○: there was slight nozzle absence.
Δ: there was nozzle absence over a wide range.
x: there was no discharge.

(48) Sharpness

The sharpness of an image after printing was observed with a naked eye.

⊙: ink smearing was not observed at all, and the image was sharp.
○: ink smearing was almost not observed, and the image was good.
Δ: slight ink smearing was observed.
x: significant ink smearing was observed.

(49) Water Resistance

The printed surface was exposed to flowing water for 1 minute, and the change in the image was observed with a naked eye.

⊙: the sharpness of the image was not changed at all.
○: although the sharpness of the image was almost not changed, slight ink smearing was observed.
Δ: the sharpness of the image was lowered, and ink smearing was observed.
x: the sharpness of the image was significantly lowered, and significant smearing was observed.

Evaluation Examples F-2 to 9 and Comparative Evaluation Examples F-10 to 13

An ink composition was prepared in the same manner as Evaluation Example F-1 except that the composition described in Table 8 is used instead. A printed matter was prepared based on the methods described above. The evaluation was made based on the methods described above. The results are shown in Table 8.

As shown in the results of the Evaluation Examples and the Comparative Evaluation Examples, it was found that the (meth)acrylamide based urethane oligomer in which a low molecular weight component like urethane adduct is contained at more than 5% by weight has poor curing property and surface dryness, and due to the low molecular weight component having high polarity, the printed matter after discharge curing shows poor water resistance. Furthermore, the urethane modified (meth)acrylate and the urethane modified (meth)acrylamide which has molecular weight and acryl equivalents that are outside a certain range exhibited poor discharge stability, and it is due to a problem in spinning property as caused by increased viscosity. Meanwhile, with the (meth)acrylate based urethane oligomer, the curing property and surface dryness were poor even when the low molecular weight component is not contained at more than 5% by weight, and, as a result, the water resistance of a printed matter after curing was also insufficient. However, with the (meth)acrylamide based urethane oligomer obtained from the present invention, it was possible to have an ink composition which has an excellent curing property and surface dryness, and also discharge stability, sharpness, and water resistance.

Evaluation Example G-1

15 parts by weight of urethane modified (meth)acrylamide synthesized in Synthesis Example 1, 50 parts by weight of "HEAA", 32 parts by weight of UNIOL D400, and 3 parts by weight of Irgacure 184 as a photopolymerization initiator were added. According to homogenous mixing, an active energy ray curable resin composition for three-dimensional object formation was prepared.

The obtained active energy ray curable resin composition for three-dimensional object formation was evaluated according to the following methods, and the results are shown in a table.

Curing Property

(50) Curing Property

A cumulative amount of light till to have complete curing of the active energy ray curable resin composition for three-dimensional object formation was measured.

⊙: completely cured at 500 mJ/cm².
○: completely cured at 500 mJ/cm² to 1000 mJ/cm².
Δ: completely cured at 1000 mJ/cm² to 3000 mJ/cm².
x: 3000 mJ/cm² or greater is required to have complete curing.

Adhesive Property Onto Polarizing Film

By using a desktop type roll laminator (RSL-382S manufactured by Royal Sovereign), 1 piece of a polarizing film is sandwiched between 2 pieces of an acryl film. Then, the active energy ray curable resin composition obtained from each Example and Comparative example was laminated between films to have thickness of 10 μm. From the top surface of the obtained laminated film, irradiation (apparatus: inverter type conveyor system ECS-4011GX manufactured by Eye Graphics Co., Ltd., metal halide lamp: M04-L41 manufactured by Eye Graphics Co., Ltd., ultraviolet illumination intensity: 700 mW/cm², cumulative amount of light: 1000 mJ/cm²) with ultraviolet rays was performed, and thus a polarizing plate having acryl film on both sides of a polarizing film was produced.

(51) Peeling Strength

Evaluation of the obtained polarizing plate was made with the same test method as above 0080.

Measurement of Rubber Hardness of Cured Product

A heavy release PET film having a thickness of 75 μm (manufactured by Toyobo Co., Ltd., polyester film E7001) was brought into close contact with a horizontally placed glass plate. A spacer having a thickness of 1 mm and an inner size of 60 mm×90 mm was installed therein. The active energy ray curable resin composition obtained in each of Examples and Comparative Examples was filled into the spacer. Thereafter, a light release PET film having a thickness of 50 μm (manufactured by Toyobo Co., Ltd., polyester film E7002) was further superimposed thereon. The active energy ray curable resin composition was cured by irradiation with a ultraviolet ray (apparatus: manufactured by Eye Graphics Co., Ltd., inverter type conveyor apparatus ECS-4011GX, metal halide lamp: M04-L41 manufactured by Eye Graphics Co., Ltd., ultraviolet illumination intensity: 300 mW/cm$^2$, cumulative amount of light in one pass: 200 mJ/cm$^2$). The pass number for ultraviolet ray irradiation was set at the pass number which has been obtained in the above 91 section. Thereafter, the release PET films on both sides were removed, and 6 pieces of the prepared cured product were overlaid. According to "Method for testing rubber hardness" of JIS K6253, Shore A hardness was measured.

(52) Bleed Out Resistance

A heavy release PET film having a thickness of 75 μm (manufactured by Toyobo Co., Ltd., polyester film E7001) was brought into close contact with a horizontally placed glass plate. A spacer having a thickness of 1 mm and an inner size of 20 mm×40 mm was installed therein. The active energy ray-curable resin composition obtained in each of Examples and Comparative Examples was filled into the spacer. Thereafter, a light release PET film having a thickness of 50 μm (manufactured by Toyobo Co., Ltd., polyester film E7002) was further superimposed thereon. The active energy ray-curable resin composition was cured by irradiation with a ultraviolet ray (apparatus: manufactured by Eye Graphics Co., Ltd., inverter type conveyor apparatus ECS-4011gX, metal halide lamp: M04-L41 manufactured by Eye Graphics Co., Ltd., ultraviolet illumination intensity: 300 mW/cm$^2$, cumulative amount of light in one pass: 200 mJ/cm$^2$). The pass number for ultraviolet ray irradiation was set at the pass number which has been obtained in the above 0121 section. Thereafter, the release PET films on both sides were removed to prepare a cured product, and the cured product was used as a test piece. The test piece was allowed to stand in a constant temperature and humidity chamber set to 25° C. and 50% RH for 168 hours. The surface of the test piece before and after standing was visually evaluated.

⊙: bleed out is not observed both before and after standing
○: although bleed out is not observed before standing, slight bleed out is observed after standing
Δ: slight bleed out is observed before standing, and bleed out is observed to some extent after standing
×: bleed out is observed to some extent before standing, and severe bleed out is observed after standing

(53) Adhesion Property

According to JIS K 5600, one hundred of squares of 1 mm×1 mm were created. Then, a cellophane tape was attached thereto, and evaluation was performed by counting the number of squares in which the coating film remained on the substrate side when the tape was peeled all at once.

Evaluation Examples G-2 to 8 and Comparative Evaluation Examples G-9 to 12

An active ray curable resin composition for three-dimensional object formation was prepared in the same manner as Evaluation Example G-1 except that the composition described in Table 9 is used instead. The evaluation was made based on the methods described above. The results are shown in Table 9.

As it is evident from the results of Table 9, the active energy ray curable resin compositions obtained from Examples G-1 to 8 have excellent coating film workability, formability, and smoothness, and exhibit a high curing property allowing curing with ultraviolet ray irradiation of 1000 mJ/cm$^2$ or less even in the presence of oxygen, and also show suppressed bleed out of a non-reactive diluent. Furthermore, they were found to exhibit a favourable adhesion property and adhesiveness to a PET substrate and a PMMA substrate, and can be suitably used as an adhesive. On the other hand, Comparative example G-9 exhibits insufficient adhesion property to a PET substrate and a PMMA substrate due to high cure shrinkage rate. Comparative example G-10 exhibits poor progress of curing, and due to insufficient film curing, a great amount of bleed out of a non-reactive diluent was shown. In addition, the adhesion property and adhesive force were also low. Comparative example G-11 exhibits insufficient curing due to high molecular weight and acryl equivalent of the oligomer in the composition, and bleed out of a non-reactive diluent has occurred. Although a favourable curing property and bleed out were shown from Comparative example G-12, the film becomes stiff after ultraviolet ray irradiation, and due to low film operability and formability and high cure shrinkage rate, the adhesion property to a plastic base is low, and thus a favourable adhesion property was not shown.

Evaluation Example H-1

40 parts by weight of urethane modified (meth)acrylamide synthesized in Synthesis Example 1, 12 parts by weight of UV3700, 20 parts by weight of "ACMO", 18 parts by weight of IBMA, 10 parts by weight of CHMA were mixed, and 3 parts by weight of Irgacure 1173 as a photopolymerization initiator were added. According to homogenous mixing, a coating agent composition for finger nail decoration was prepared.

Method for Finger Nail Decoration

The obtained coating agent composition for finger nail decoration was evenly applied on top of a finger nail by using a flat brush. According to irradiation with a UV illuminator (36 W), which is exclusively used for gel nail, for 60 seconds, finger nail decoration was formed on top of a finger nail.

(54) Curing Property

By touching the surface of the finger nail decoration which has been obtained by the above method with a finger, stickiness state was evaluated.

⊙: there is no stickiness at all.
○: although there is slight stickiness, a finger mark does not remain on the surface.
Δ: there is stickiness, and a finger mark remains on the surface.
×: stickiness is severe, and a finger sticks to the surface.

(55) Smoothness

The surface of the finger nail decoration which has been obtained by the above method was observed with a naked eye.

⊙: surface is smooth, and no irregularities are observed from any part of the coated surface.
○: overall smoothness is observed, but some irregularities are observed.
Δ: brush marks of a flat brush partially remain after the application.
×: brush marks of a flat brush remain after the application.

(56) Glossiness

The surface of the finger nail decoration which has been obtained by the above was observed with a naked eye.

⊙: there is surface glossiness.

○: light reflection can be confirmed, but slight opaqueness is shown.

Δ: overall, surface is slightly opaque.

×: surface is opaque.

(57) Adhesion Property

The finger nail decoration which has been obtained by the above was scratched with other finger nail. Thereafter, a change in the outer appearance in the finger nail decoration was determined with a naked eye.

⊙: there is no change in the outer appearance.

○: slight floating is shown in part of the finger nail decoration, and whitening is found.

Δ: peeling is found from part of the finger nail decoration.

×: significant peeling of the finger nail decoration is found.

(58) Removability

Cotton containing acetone was applied such that it can cover the finger nail decoration which has been obtained by the above method. Next, after wearing saniment gloves, the finger nail fully covered with aluminum foil was allowed to be immersed in hot water for 10 minutes. After removing the aluminum foil and cotton, the finger nail was briefly rubbed by using cloth.

⊙: finger nail decoration can be easily peeled even without using the cloth.

○: finger nail decoration can be easily peeled when gentle rubbing using cloth is carried out.

Δ: finger nail decoration can be peeled when rubbing is continued for 1 minute or so by using cloth.

×: acetone swelling does not occur, and peeling cannot be achieved even after rubbing with cloth.

Evaluation Examples H-2 to 8 and Comparative Evaluation Examples H-9 to 12

A coating agent composition for nail decoration was prepared in the same manner as Evaluation Example H-1 except that the composition described in Table 10 is used instead. Nail decoration was produced based on the methods described above. The evaluation was made based on the methods described above. The results are shown in Table 10.

As shown in the results of the Evaluation Examples and the Comparative Evaluation Examples, in a case where the urethane modified (meth)acrylamide which has molecular weight and acryl equivalents that are outside a certain range or the urethane modified (meth)acrylate are blended, the curing property of the composition and glossiness of the obtained decorated film were low. Furthermore, coating film unevenness caused by high viscosity yields poor smoothness at the time of forming a finger nail decoration on a finger nail, resulting in the liquid flow marks and brush marks of a flat brush. Furthermore, as the cure shrinkage rate is high, the adhesion property is deteriorated. In addition, with the (meth)acrylamide based urethane oligomer in which the low molecular weight component is contained at more than 5% by weight or with the acrylate based urethane oligomer, the curing property was relatively high, but a decrease in the adhesion property was shown as caused by high cure shrinkage. On the other hand, when the urethane modified (meth) acrylamide of the present invention is used, stickiness of a decorative film after curing is suppressed, and, due to low cure shrinkage, it was possible to form finger nail decoration which has high adhesion with no floating from the finger nail and also high removability with acetone.

Evaluation Example I-1

25 parts by weight of urethane modified (meth)acrylamide based H-1 synthesized in Synthesis Example 1, 35 parts by weight of Light acrylate PE-4, 15 parts by weight of "ACMO", and 25 parts by weight of DPHA were mixed, and 3 parts by weight of Darocur 1173 as a photopolymerization initiator and 3 parts by weight of 8019add as a surface modifying agent were added. According to homogenous mixing, a composition for protecting car exterior was prepared.

Method for Producing Film for Protecting Car Exterior

On a surface of a polycarbonate resin plate (15 cm×15 cm), coating was performed with a bar coater such that the coating film after drying is about 10 μm. After drying for 15 minutes by using a hot air dryer at 90° C., irradiation with a ultraviolet ray was carried out (apparatus: manufactured by Eye Graphics Co., Ltd., inverter type conveyor apparatus ECS-4011GX, metal halide lamp: M04-L41 manufactured by Eye Graphics Co., Ltd., ultraviolet illumination intensity: 700 mW/cm², cumulative amount of light: 1000 mJ/cm²) to prepare a sample which has a cured film on a resin plate.

Evaluation was made in the same test method as above 0101.

(59) Weather Resistance

Based on JIS KS5400, an acceleration test was carried out for 5000 hours using a carbon arc type sunshine weather meter. A decrease in the adhesion property and presence or absence of cracks was evaluated every 500 hours. Furthermore, with regard to the adhesion property, when a cellophane tape adhered on a test film is peeled off but the film is not detached from the base, it is determined as "good". Cracks were determined with a naked eye, and, when there is no occurrence of cracks, it is determined as "good". The evaluation results are evaluated based on the following four levels. Namely, the period in which a decrease in the adhesion property and cracks are confirmed is determined as follows:

⊙: 5000 hours or longer

○: 4000 hours or longer but shorter than 5000 hours

Δ: 3000 hours or longer but shorter than 4000 hours

×: 3000 hours or shorter

(60) Water Resistance

On a polycarbonate rein plate, a 20 μm thick ultraviolet ray cured film was prepared, and surface drying was carried out for 10 minutes at 70° C. Subsequently, the sensitivity for water expansion was evaluated. The evaluation results are evaluated based on the following four levels depending on the degree of influence.

⊙: no influence

○: film is very slightly dissolved

Δ: film is partly dissolved

×: film is completely dissolved

(61) Adhesion Property

A film for protecting car exterior was used, and, according to JIS K 5600, one hundred of squares of 1 mm×1 mm were created. Then, a cellophane tape was attached thereto, and evaluation was performed by counting the number of squares in which the coating film remained on the substrate side when the tape was peeled all at once.

(62) Abrasion Resistance

According to ASTM D-1044, a taper type abrasion test was carried out.

Evaluation was made by measuring haze difference ΔH (%) before and after the taper type abrasion test. Herein, the abrasion wheel was CS-10F, load was 500 g for each, and revolution number was 500 times. Transparency was evaluated according to the following four levels.

⊙: haze difference ΔH was less than 7%
○: haze difference ΔH was 7% or more but less than 10%
Δ: haze difference ΔH was 10% or more but less than 15%
×: haze difference ΔH was 15% or more

(63) Scratch Resistance

Evaluation was made in the same test method as above 0095.

Evaluation Examples 1-2 to 8 and Comparative Evaluation Examples 1-9 to 12

Production was made in the same manner as Evaluation Example I-1 except that the composition described in Table 11 is used instead. A film for protecting car exterior was produced based on the methods described above. The evaluation was made based on the methods described above. The results are shown in Table 11.

As shown in the results of the Evaluation Examples and the Comparative Evaluation Examples, in a case where the urethane modified (meth)acrylamide which has molecular weight, acryl equivalents, and viscosity that are outside a certain range, or the urethane modified (meth)acrylate, or an oligomer in which low molecular products are contained at 5% or more are formulated, there was a decrease in the curing property, tack property, and shrinkage resistance of a composition, and thus the water resistance and adhesion property of the obtained protective film were low, and a deterioration in transparency, which is caused by poor compatibility, was shown. On the other hand, when the urethane modified (meth)acrylamide of the present invention is used, it was possible to obtain a protective film which has an excellent curing property after curing, high adhesion with no floating due to low cure shrinkage while having high crosslinking density, and also excellent abrasion resistance and dent resistance.

Evaluation Example J-1

60 parts by weight of urethane modified (meth)acrylamide UT-1 synthesized in Synthesis Example 1, 5 parts by weight of urethane modified (meth)acrylamide UT-2 synthesized in Synthesis Example 2, 11 parts by weight of HDDA, 20 parts by weight of DPHA, 4 parts by weight of IBOA, and 10 parts by weight of Silica microparticles IPL-ST-L were mixed, and 50 parts by weight of MEK as a solvent and 3 parts by weight of Irgacure 184 as a photopolymerization initiator were added. According to homogenous mixing with 50 parts of MEK, a resin composition for decorative film was prepared.

Method for Producing Photocuring Type Decorative Film

The obtained resin composition for decorative film was applied on a PET film ("Softshine TA009" manufactured by Toyobo Co., Ltd.) having a thickness of 125 μm using a bar coater (RDS 30) such that the thickness of the dried film became 20 μm. Thereafter, according to drying for 1 minute at 100° C., a molded film before ultraviolet ray curing was prepared. After that, according to ultraviolet ray irradiation (ultraviolet illumination intensity: 2 mW/cm², cumulative amount of light: 50 mJ/cm²), a decorative film in semi-cured state was produced. Each of the molded film and the decorative film in semi-cured state was evaluated according to the following methods. The results are shown in Table 12.

(64) Transparency

The obtained molded film in semi-cured state was used, and evaluation was made in the same test method as above 0101.

(65) Blocking Resistance

On top of the molded film in semi-cured state, a non-treated PET ("Cosmoshine A4100" manufactured by Toyobo Co., Ltd., one side was not anchor-coat-treated, having a thickness of 100 μm) was overlaid. By reciprocally moving two times a pressure roller of a load of 2 kg on top of the non-treated PET, pressure-adhesion was performed, and the resulting product was allowed to stand for 30 minutes in an environment with temperature of 23° C. and humidity of 50%. Thereafter, the non-treated PET was peeled off. Blocking resistance was then evaluated according to a naked eye observation.

⊙: There is no adhesion to the non-treated PET, and no change in the outer appearance of the molded film.
○: There is no adhesion to the non-treated PET, but marks remain on part of the surface of the molded film.
Δ: There is no migration to the non-treated PET, but marks remain on the entire surface of the molded film.
×: There is migration to the non-treated PET, and peeling or floating is shown on the surface of the molded film.

(66) Elongation at Break

Measurement was performed, at a temperature of 130° C. and speed of 10 mm/min, by using the molded film in semi-cured state which has been obtained in the above.

Device for measurement; Tensilon Universal Tester RTA-100 (manufactured by Orientec Co., Ltd.)

Elongation at break [%]=Sheet length at break/Sheet length before test×100

⊙: elongation at break is 100% or higher
○: elongation at break is 50% or higher but lower than 100%
Δ: elongation at break is 10% or higher but lower than 50%
×: elongation at break is lower than 10%

(67) Molding Processability Test

The obtained molded film in semi-cured state was subjected to molding processing at heating temperature of 130° C. by using a pressure molding machine SDF400 (manufactured by Sodick Co., Ltd.). After cooling to 25° C., the state of the decorative layer of the molded article was determined with a naked eye.

⊙: absolutely no fissure is observed, and the surface has high transparency.
○: although no fissure is observed, there is unevenness in thickness of a decorative layer, thus showing partial decrease in transparency.
Δ: fissure or slight cracks are observed, and unevenness in thickness of a decorative layer or a decrease in transparency is observed.
×: many cracks are observed, and unevenness in thickness of a decorative layer or a decrease in transparency is significant.

(68) Curing Property

The coated resin composition for decorative film was dried for 1 minute at 100° C. After that, the obtained coating film was irradiated with ultraviolet rays of ultraviolet illumination intensity of 700 mW/cm², and the cumulative amount of light till to have complete curing of the resin composition was measured. The complete curing means a state in which, when the surface of the cured film is rubbed with silicone rubber, no trace is present.
⊙: completely cured at a cumulative amount of light of 1000 mJ/cm$^2$.
◯: completely cured at a cumulative amount of light of 1000 mJ/cm$^2$ to 2,000 mJ/cm$^2$.
Δ: completely cured at a cumulative amount of light of 2,000 mJ/cm$^2$ to 5,000 mJ/cm$^2$.
×: a cumulative amount of light of 5,000 mJ/cm$^2$ or greater is required to have complete curing.
(69) Adhesion Property According to JIS K 5600, one hundred of squares of 1 mm×1 mm were created by using the obtained decorative film. Then, a cellophane tape was attached thereto, and evaluation was performed by counting the number of squares in which the coating film remained on the substrate side when the tape was peeled all at once.
(70) Pencil Hardness The evaluation was carried out based on JIS K 5600 by using the obtained decorative film. Namely, when the decorative film was scratched by a pencil for 10 mm or so at an angle of 45°, the hardness of the hardest pencil not yielding any scratches on a surface of the decorative film was determined as pencil hardness.
⊙: pencil hardness is 2H or higher
◯: pencil hardness is HB to H
Δ: pencil hardness is 3B to B
×: pencil hardness is 4B or lower
(71) Scratch Resistance Steel wool of #0000 was reciprocally moved on the decorative film ten times while a load of 200 g/cm$^2$ was applied, and the presence of an occurrence of scratches was evaluated with a naked eye.
⊙: peeling of a film or occurrence of scratches is hardly observed.
◯: fine scratches are slightly observed on a part of a film.
Δ: streaky scratches are observed on the entire film surface.
×: peeling of a film occurs.
(72) Bending Resistance The decorative film obtained in the above was bent such that the coating surface faces the outside. After applying a pressurizing stone of 1 kg thereto, it was allowed to stand for 10 minutes. Then, the presence or absence of cracks on a surface of the decorative film was observed with a naked eye.
⊙: absolutely no cracks were observed.
◯: bent part was partially whitened.
Δ: cracks were observed from part of the bent part.
×: cracks were observed from the bent part.

Evaluation Examples J-2 to 8 and Comparative Evaluation Examples J-9 to 12

A resin composition for decorative film was prepared in the same manner as Evaluation Example J-1 except that the composition described in Table 12 is used instead. A decorative film was produced according to the methods described above. The evaluation was made based on the methods described above. The results are shown in Table 12.

As shown in the results of the Evaluation Examples and the Comparative Evaluation Examples, in a case where the urethane modified (meth)acrylamide which has molecular weight, acryl equivalents, and viscosity that are outside a certain range, and the urethane modified (meth)acrylate are blended, as the curing property of a molded film in semi-cured state is low and tack is shown and the blocking resistance is poor, and thus there was a tendency that it is difficult to obtain the elongation at high temperature conditions. There was also a problem that the obtained decorative film has a poor adhesion property for various plastic substrates. Furthermore, the oligomer containing 5% or more of low molecular products has poor transparency, and thus cannot be used. On the other hand, when the urethane modified (meth)acrylamide of the present invention is used, as a hard segment with excellent curing property and similar aggregation between the amide group and urethane bond is formed, a molded film before ultraviolet curing which exhibits high blocking resistance and molding processability and has no cracks was obtained. Furthermore, the similar aggregative force is a cause of achieving the low curing shrinkage property, and it was possible to obtain a photo-curing type decorative film which has a favourable adhesion property to various plastic substrates.

TABLE 1

| | | | Evaluation Example | | | | | | | | | | |
|---|---|---|---|---|---|---|---|---|---|---|---|---|---|
| | | | UT-1 | UT-2 | UT-3 | UT-4 | UT-5 | UT-6 | UT-7 | UT-8 | UT-9 | UT-10 |
| Characteristics of oligomer | Compatibility | IPA | ◯ | ⊙ | ⊙ | ⊙ | ⊙ | ⊙ | ⊙ | ⊙ | ⊙ | ◯ |
| | | MEK | ⊙ | ⊙ | ⊙ | ⊙ | Δ | ⊙ | ⊙ | ⊙ | ⊙ | ⊙ |
| | | THF | ⊙ | ⊙ | ⊙ | ⊙ | ⊙ | ⊙ | ⊙ | ⊙ | ⊙ | ⊙ |
| | | Ethyl acetate | ⊙ | ⊙ | ⊙ | ⊙ | ⊙ | ⊙ | ⊙ | ⊙ | ⊙ | ⊙ |
| | | Toluene | ⊙ | ⊙ | ⊙ | ◯ | ⊙ | ⊙ | ⊙ | ⊙ | ⊙ | ⊙ |
| | | ACMO | ⊙ | ⊙ | ⊙ | ⊙ | ⊙ | ◯ | Δ | ⊙ | ⊙ | ⊙ |
| | | HDDA | ⊙ | ⊙ | ⊙ | ⊙ | Δ | ⊙ | ⊙ | Δ | ⊙ | ⊙ |
| | | BA | ⊙ | ⊙ | ⊙ | ⊙ | ◯ | ⊙ | ⊙ | ⊙ | ⊙ | ⊙ |
| | | IBOA | ⊙ | ⊙ | ⊙ | ⊙ | Δ | ⊙ | ◯ | Δ | ⊙ | ⊙ |
| | | 2EHA | ⊙ | ⊙ | ⊙ | ⊙ | Δ | ⊙ | ⊙ | ⊙ | ⊙ | ⊙ |
| | | THFA | ⊙ | ⊙ | ⊙ | ⊙ | ⊙ | ⊙ | ⊙ | ⊙ | ⊙ | ⊙ |

| | | | Evaluation Example | | | | | | Comparative Evaluation Example | | | |
|---|---|---|---|---|---|---|---|---|---|---|---|---|
| | | | UT-11 | UT-12 | UT-13 | UT-14 | UT-15 | UT-16 | UA-1 | UA-2 | UA-3 | UA-4 |
| Characteristics of oligomer | Compatibility | IPA | ⊙ | ⊙ | ⊙ | ⊙ | ⊙ | ⊙ | ⊙ | ◯ | ◯ | ◯ |
| | | MEK | ⊙ | ⊙ | ⊙ | ⊙ | ⊙ | ⊙ | ⊙ | ⊙ | ⊙ | Δ |
| | | THF | ⊙ | ⊙ | ⊙ | ⊙ | ⊙ | ⊙ | ⊙ | ⊙ | ⊙ | Δ |

TABLE 1-continued

| | | | | | | | | | | |
|---|---|---|---|---|---|---|---|---|---|---|
| Ethyl acetate | ⊙ | ⊙ | ⊙ | ⊙ | ⊙ | ⊙ | ○ | ⊙ | ⊙ | Δ |
| Toluene | ⊙ | ⊙ | Δ | ⊙ | ○ | Δ | X | ○ | ⊙ | X |
| ACMO | ⊙ | ⊙ | ⊙ | ⊙ | Δ | Δ | Δ | Δ | Δ | X |
| HDDA | ○ | ⊙ | ⊙ | ⊙ | ○ | Δ | Δ | Δ | Δ | X |
| BA | ⊙ | ⊙ | ⊙ | ⊙ | ⊙ | ⊙ | X | Δ | ⊙ | Δ |
| IBOA | ○ | ⊙ | ○ | ○ | ○ | Δ | X | X | X | X |
| 2EHA | ⊙ | ⊙ | ⊙ | ⊙ | ⊙ | ○ | X | X | ⊙ | X |
| THFA | ⊙ | ⊙ | ⊙ | ⊙ | ○ | Δ | X | X | ⊙ | Δ |

TABLE 2

| | | Evaluation Example | | | | | | | | | | | | | | | | Comparative Evaluation Example | | | |
|---|---|---|---|---|---|---|---|---|---|---|---|---|---|---|---|---|---|---|---|---|---|
| | | A-1 | A-2 | A-3 | A-4 | A-5 | A-6 | A-7 | A-8 | A-9 | A-10 | A-11 | A-12 | A-13 | A-14 | A-15 | A-16 | A-17 | A-18 | A-19 | A-20 |
| Urethane oligomer | UT-1 | 100 | | | | | | | | | | | | | | | | | | | |
| | UT-2 | | 100 | | | | | | | | | | | | | | | | | | |
| | UT-3 | | | 100 | | | | | | | | | | | | | | | | | |
| | UT-4 | | | | 100 | | | | | | | | | | | | | | | | |
| | UT-5 | | | | | 100 | | | | | | | | | | | | | | | |
| | UT-6 | | | | | | 100 | | | | | | | | | | | | | | |
| | UT-7 | | | | | | | 100 | | | | | | | | | | | | | |
| | UT-8 | | | | | | | | 100 | | | | | | | | | | | | |
| | UT-9 | | | | | | | | | 100 | | | | | | | | | | | |
| | UT-10 | | | | | | | | | | 100 | | | | | | | | | | |
| | UT-11 | | | | | | | | | | | 100 | | | | | | | | | |
| | UT-12 | | | | | | | | | | | | 100 | | | | | | | | |
| | UT-13 | | | | | | | | | | | | | 100 | | | | | | | |
| | UT-14 | | | | | | | | | | | | | | 100 | | | | | | |
| | UT-15 | | | | | | | | | | | | | | | 100 | | | | | |
| | UT-16 | | | | | | | | | | | | | | | | 100 | | | | |
| | UA-1 | | | | | | | | | | | | | | | | | 100 | | | |
| | UA-2 | | | | | | | | | | | | | | | | | | 100 | | |
| | UA-3 | | | | | | | | | | | | | | | | | | | 100 | |
| | UA-4 | | | | | | | | | | | | | | | | | | | | 100 |
| Photopolymerization initiator | Irgacure1173 | 3 | 3 | 3 | 3 | 3 | 3 | 3 | 3 | 3 | 3 | 3 | 3 | 3 | 3 | 3 | 3 | 3 | 3 | 3 | 3 |
| Characteristics of cured product | Curing property | ⊙ | ○ | ⊙ | ⊙ | ⊙ | ⊙ | ⊙ | ⊙ | ⊙ | ⊙ | ⊙ | ⊙ | ⊙ | ⊙ | ⊙ | ⊙ | ⊙ | △ | △ | ⊙ |
| | Tack resistance | ○ | ○ | ○ | ○ | ⊙ | ○ | ○ | ○ | ○ | ○ | ○ | ○ | ○ | ○ | ○ | ○ | ⊙ | △ | △ | ○ |
| | Shrinkage resistance | ○ | ○ | ○ | ○ | ○ | ○ | ○ | ○ | ○ | ○ | ○ | ○ | ○ | ○ | ○ | △ | X | X | ⊙ | X |
| | Transparency | ⊙ | ⊙ | ⊙ | ⊙ | ⊙ | ⊙ | ⊙ | ⊙ | ⊙ | ⊙ | ⊙ | ⊙ | ⊙ | ⊙ | ⊙ | ⊙ | X | ⊙ | ⊙ | △ |
| | Water absorption ratio [%] | 1.1 | 0.7 | 2.6 | 2.3 | 0.7 | 0.5 | 0.2 | 1.3 | 1.1 | 1.3 | 1.6 | 2.5 | 2.9 | 2.0 | 1.8 | 1.3 | 2.4 | 4.3 | 3.9 | 3.8 |
| | Adhesion property PET (easy adhesion) | 100/100 | 100/100 | 100/100 | 100/100 | 100/100 | 100/100 | 100/100 | 100/100 | 100/100 | 100/100 | 100/100 | 100/100 | 100/100 | 100/100 | 100/100 | 100/100 | 90/50 | 70/100 | 80/100 | 50/100 |
| | PET (non-treated) | 80/100 | 70/100 | 80/100 | 80/100 | 80/100 | 100/100 | 100/100 | 100/100 | 100/100 | 100/100 | 80/100 | 70/100 | 70/100 | 100/100 | 100/100 | 70/100 | 100/0 | 100/50 | 100/60 | 100/0 |
| | PC | 70/100 | 100/100 | 80/100 | 80/100 | 90/100 | 90/100 | 100/100 | 90/100 | 90/100 | 80/100 | 70/100 | 50/100 | 50/100 | 60/100 | 100/100 | 50/100 | 100/0 | 100/50 | 100/60 | 100/0 |
| | PMMA | 100/100 | 70/100 | 70/100 | 80/100 | 100/100 | 70/100 | 70/100 | 70/100 | 60/100 | 70/100 | 70/100 | 50/100 | 60/100 | 60/100 | 100/100 | 40/100 | 100/0 | 100/30 | 100/30 | 100/0 |
| | Strength at break [N/25 mm²] | 25 | 13 | 15 | 22 | 18 | 23 | 30 | 35 | 20 | 27 | 50 | 13 | 17 | 14 | 23 | 23 | 34 | 30 | 10 | 15 |
| | Elongation at break [%] | 180 | 250 | 220 | 280 | 150 | 230 | 250 | 170 | 190 | 180 | 50 | 170 | 140 | 200 | 160 | 60 | 10 | 60 | 170 | 6 |

TABLE 3

|  |  | Evaluation Example |  |  |  |  |  |  |  |  | Comparative Evaluation Example |  |  |  |
|---|---|---|---|---|---|---|---|---|---|---|---|---|---|---|
|  |  | B-1 | B-2 | B-3 | B-4 | B-5 | B-6 | B-7 | B-8 | B-9 | B-10 | B-11 | B-12 | B-13 |
| Urethane oligomer | UT-1 | 25 | | | | | | | | | | | | |
|  | UT-2 | | 52 | | | | | | | | | | | |
|  | UT-3 | | | 25 | | | | | | | | | | |
|  | UT-4 | | | | 12 | | | | | | | | | |
|  | UT-5 | | | | | 20 | | | | | | | | |
|  | UT-6 | | | | | | 39 | | | | | | | |
|  | UT-7 | | | | | | | 10 | | | | | | |
|  | UT-12 | | | | | | | | 40 | | | | | |
|  | UA-1 | | | | | | | | | 51 | | | | |
|  | UA-2 | | | | | | | | | | 47 | | | |
|  | UA-3 | | | | | | | | | | | 20 | 40 | |
|  | UA-4 | | | | | | | | | | | | | 50 |
| Other monomers | "HEAA" | 10 | | 20 | 28 | 10 | | 20 | 10 | 12 | 10 | 13 | 20 | 18 |
|  | "DEAA" | 40 | 18 | 28 | 30 | 10 | 18 | 10 | 10 | | 10 | 10 | 22 | 29 |
|  | 2EHA | 9 | 22 | 14 | 9 | 52 | 20 | 50 | 30 | 20 | 30 | 52 | 15 | |
|  | CHA | 15 | 8 | 10 | 18 | | | | 5 | | | 10 | | |
|  | EEA | | | | | | 15 | 5 | | 12 | | | | |
| Ionic vinyl monomer | DMAEA-TFSIQ | 1 | | | | 3 | 8 | 5 | 5 | 5 | 3 | 3 | 3 | 3 |
|  | DMAPAA-TFSIQ | | | | | 5 | | | | | | | | |
| Photopolymerization initiator | Irgacure184 | 3 | 3 | 3 | 3 | 3 | 3 | 3 | 3 | 3 | 3 | 3 | 3 | 3 |
| Characteristics of cohesive sheet | Transparency | 100 | 100 | 100 | 100 | 100 | 100 | 100 | 100 | 100 | 80 | 100 | 100 | 70 |
|  | Surface resistivity [Ω/□] | $5.5 \times 10^{12}$ | $2.3 \times 10^{13}$ | $8.2 \times 10^{11}$ | $7.8 \times 10^{11}$ | $1.2 \times 10^{10}$ | $9.3 \times 10^{10}$ | $3.2 \times 10^{9}$ | $1.6 \times 10^{10}$ | $3.6 \times 10^{11}$ | $3.2 \times 10^{10}$ | $8.1 \times 10^{11}$ | $8.8 \times 10^{10}$ | $8.8 \times 10^{13}$ |
|  | Cohesive force PET | ⊙ | ⊙ | ⊙ | ⊙ | ⊙ | ⊙ | ⊙ | ⊙ | ⊙ | △ | ○ | △ | △ |
|  | Glass | ⊙ | ⊙ | ⊙ | ⊙ | ⊙ | ⊙ | ⊙ | ⊙ | ⊙ | △ | ○ | △ | × |
|  | Contamination resistance PET | ⊙ | ○ | ○ | ○ | ○ | ○ | ○ | ○ | ○ | × | ○ | △ | × |
|  | Glass | ⊙ | ○ | ○ | ○ | ○ | ○ | ○ | ○ | ○ | × | × | △ | × |
|  | Yellowing resistance | ⊙ | ⊙ | ⊙ | ⊙ | ⊙ | ⊙ | ⊙ | ⊙ | ⊙ | △ | ○ | ⊙ | × |
|  | Moisture and heat resistance | ⊙ | ⊙ | ⊙ | ⊙ | ⊙ | ⊙ | ⊙ | ⊙ | ⊙ | × | ⊙ | ○ | × |
|  | Step followability | ⊙ | ⊙ | ⊙ | ⊙ | ⊙ | ⊙ | ⊙ | ⊙ | ⊙ | × | △ | × | × |
|  | Punching processability | ○ | ⊙ | ○ | ○ | ○ | ○ | ○ | ○ | ○ | × | △ | × | × |

TABLE 3-2

|  |  | Evaluation Example | | | | | Comparative Evaluation Example | |
|---|---|---|---|---|---|---|---|---|
|  |  | B-14 | B-15 | B-16 | B-17 | B-18 | B-19 | B-20 |
| Urethane oligomer | UT-7 | 40 |  |  |  |  |  |  |
|  | UT-8 |  | 70 |  |  |  |  |  |
|  | UT-9 |  |  | 60 |  |  |  |  |
|  | UT-10 |  |  |  | 50 |  |  |  |
|  | UT-5 |  |  |  |  |  |  |  |
|  | UT-11 |  |  |  |  | 70 |  |  |
|  | UA-1 |  |  |  |  |  | 70 |  |
|  | UA-2 |  |  |  |  |  |  | 70 |
| Other monomers | "HEAA" | 15 | 10 | 5 |  | 10 |  |  |
|  | "DEAA" | 15 |  | 10 | 10 | 10 |  | 10 |
|  | 2EHA | 30 |  | 15 | 30 |  | 10 |  |
|  | CHA |  | 20 |  | 5 | 10 |  | 10 |
|  | EEA |  |  | 10 | 5 |  | 20 | 10 |
| Ionic vinyl monomer | DMAEA-TFSIQ |  |  |  |  |  |  |  |
| DMAPAA-TFSIQ |  | 3 | 3 | 3 | 3 | 3 | 3 | 3 |
| Photopolymerization initiator | Irgacure184 | 3 | 3 | 3 | 3 | 3 | 3 | 3 |
| Characteristics of cohesive sheet | Transparency | 100 | 100 | 100 | 100 | 100 | 50 | 100 |
|  | Surface resistivity [Ω/□] | $3.6 * 10^{13}$ | $3.6 * 10^{12}$ | $4.6 * 10^{13}$ | $9.8 * 10^{12}$ | $2.8 * 10^{11}$ | $3.6 * 10^{12}$ | $8.8 * 10^{13}$ |
|  | Cohesive force  PET | ⊙ | ⊙ | ⊙ | ⊙ | ⊙ | Δ | ○ |
|  | Copper | ⊙ | ⊙ | ○ | ⊙ | ⊙ | X | X |
|  | Glass | ○ | ○ | ⊙ | ⊙ | ⊙ | Δ | X |
|  | Yellowing resistance | ⊙ | ○ | ○ | ⊙ | ○ | Δ | ⊙ |
|  | Presence or absence of air bubbles | ⊙ | ⊙ | ⊙ | ⊙ | ⊙ | X | X |
|  | Recognisability | ⊙ | ⊙ | ⊙ | ⊙ | ⊙ | X | X |

TABLE 4

|  |  | Evaluation Example | | | | | | | | | Comparative Evaluation Example | | | |
|---|---|---|---|---|---|---|---|---|---|---|---|---|---|---|
|  |  | C-1 | C-2 | C-3 | C-4 | C-5 | C-6 | C-7 | C-8 | C-9 | C-10 | C-11 | C-12 | C-13 |
| Urethane oligomer | UT-1 | 25 | 37 |  |  |  |  |  |  |  |  |  |  |  |
|  | UT-2 |  |  | 24 |  |  |  |  |  |  |  |  |  |  |
|  | UT-3 |  |  | 10 | 33 |  |  |  |  |  |  |  |  |  |
|  | UT-4 |  | 10 |  |  | 30 |  |  |  |  |  |  |  |  |
|  | UT-5 |  |  |  |  |  |  |  |  |  |  |  |  |  |
|  | UT-5 |  |  |  |  |  | 30 |  |  |  |  |  |  |  |
|  | UT-6 |  |  |  |  |  |  | 20 |  |  |  |  |  |  |
|  | UT-7 |  |  |  |  |  |  |  | 25 |  |  |  |  |  |
|  | UT-8 |  |  |  |  |  |  |  |  | 50 |  |  |  |  |
|  | UT-9 |  |  |  |  |  |  |  |  |  |  |  |  |  |
|  | UA-1 |  |  |  |  |  |  |  |  |  | 50 |  |  |  |
|  | UA-2 |  |  |  |  |  |  |  |  |  |  | 26 |  |  |
|  | UA-3 |  |  |  |  |  |  |  |  |  |  |  | 45 |  |
|  | UA-4 |  |  |  |  |  |  |  |  |  |  |  |  | 40 |
| Other monomers | "ACMO" | 15 | 15 | 20 | 15 | 20 | 20 | 30 | 30 | 30 | 20 | 22 | 17 | 20 |
|  | "HEAA" |  | 20 | 35 |  |  |  | 15 | 10 |  | 20 | 17 |  | 10 |
|  | "DMAA" | 20 |  |  | 20 |  |  |  | 10 |  |  | 14 | 8 | 10 |
|  | "DMAPAA" |  | 10 |  |  |  |  | 10 |  |  | 10 |  |  |  |
|  | HEA | 25 |  |  | 25 | 30 | 30 |  | 25 | 20 |  |  | 20 |  |
|  | THFA | 15 |  | 5 | 7 |  |  |  |  |  |  | 10 | 10 |  |
|  | IBOA |  | 8 | 6 |  | 20 | 20 | 25 |  |  |  | 11 |  | 20 |
| Photopolymerization initiator | Irgacure1173 | 3 | 3 | 3 | 3 | 3 | 3 | 3 | 3 | 3 |  | 3 | 3 | 3 |
| Characteristics of adhesive | Observation of surface shape | ⊙ | ⊙ | ⊙ | ⊙ | ⊙ | ⊙ | ⊙ | ⊙ | ⊙ | ⊙ | ⊙ | X | ○ |
|  | Peeling strength | ⊙ | ⊙ | ⊙ | ⊙ | ⊙ | ⊙ | ⊙ | ⊙ | ⊙ | ⊙ | Δ | X | ⊙ |
|  | Water resistance | ○ | ○ | ○ | ○ | ○ | ○ | ○ | ○ | ○ | X | X | ○ | X |
|  | Durability | ⊙ | ⊙ | ○ | ○ | ○ | ○ | ⊙ | ⊙ | ⊙ | X | X | Δ | Δ |

TABLE 5

| | | | Evaluation Example | | | | | | | | Comparative Evaluation Example | | | |
|---|---|---|---|---|---|---|---|---|---|---|---|---|---|---|
| | | | D-1 | D-2 | D-3 | D-4 | D-5 | D-6 | D-7 | D-8 | D-10 | D-11 | D-12 | D-13 |
| Urethane oligomer | | UT-1 | 23 | | | | | | | | | | | |
| | | UT-2 | | 22 | | | | | | | | | | |
| | | UT-3 | | | 47 | | | | | | | | | |
| | | UT-4 | | | | 40 | | | | | | | | |
| | | UT-5 | | | | | | | | | | | | |
| | | UT-5 | | | | | 46 | | | | | | | |
| | | UT-6 | | | | | | 30 | | | | | | |
| | | UT-7 | | | | | | | 60 | | | | | |
| | | UT-8 | | | | | | | | 45 | | | | |
| | | UA-1 | | | | | | | | | 40 | | | |
| | | UA-2 | | | | | | | | | | 24 | | |
| | | UA-3 | | | | | | | | | | | 38 | |
| | | UA-4 | | | | | | | | | | | | 32 |
| | | UV-7600B | 16 | 30 | 12 | | | 20 | | | 10 | 25 | 20 | 30 |
| Polyfunctional acrylate | | PETA | 20 | 8 | | 10 | 10 | | | | 20 | | | |
| | | DPHA | 12 | | 13 | | 10 | 20 | 18 | | | 17 | 18 | |
| Other monomers | | "ACMO" | 17 | 5 | 20 | 20 | | 18 | 12 | | 12 | | 10 | 13 |
| | | "DMAA" | | 15 | | 10 | 22 | | | | 8 | 4 | | 20 |
| | | THFA | 12 | | | | 7 | | 10 | | | | 14 | |
| | | IBOA | | 20 | 8 | 20 | | 12 | | | 10 | 10 | | |
| Solvent | | MEK | | | | | | | 10 | | | | | |
| Photopolymerization initiator | | Irgacure1173 | 3 | 3 | 3 | 3 | 3 | 3 | 3 | 3 | 3 | 3 | 3 | 3 |
| Characteristics of coating film | | Compatibility | ⊙ | ⊙ | ⊙ | ⊙ | ⊙ | ⊙ | ⊙ | ⊙ | Δ | ⊙ | ⊙ | X |
| | Wettability | PET (easy adhesion) | ⊙ | ⊙ | ⊙ | ⊙ | ⊙ | ⊙ | ⊙ | ⊙ | ○ | ⊙ | Δ | Δ |
| | | PET (non-treated) | ⊙ | ⊙ | ⊙ | ⊙ | ⊙ | ⊙ | ⊙ | ○ | Δ | Δ | Δ | Δ |
| | | PC | ○ | ⊙ | ⊙ | ⊙ | ⊙ | ⊙ | ⊙ | ⊙ | ○ | ⊙ | Δ | Δ |
| | | PMMA | ⊙ | ⊙ | ⊙ | ⊙ | ⊙ | ○ | ⊙ | ○ | Δ | Δ | Δ | Δ |
| | Curing property | | ⊙ | ⊙ | ⊙ | ⊙ | ⊙ | ⊙ | ⊙ | ⊙ | ⊙ | Δ | ○ | ⊙ |
| | Tack resistance | | ○ | ○ | Δ | ○ | ⊙ | ⊙ | ○ | ○ | ⊙ | Δ | Δ | ⊙ |
| | Shrinkage resistance | | ⊙ | ⊙ | ⊙ | ⊙ | ⊙ | ⊙ | ⊙ | Δ | X | X | ○ | X |
| | Scratch resistance | | ○ | ○ | ○ | ○ | ○ | ○ | ○ | ⊙ | ⊙ | Δ | Δ | ⊙ |
| | Self restoring property | | ⊙ | ○ | ○ | ○ | ⊙ | ⊙ | ⊙ | ⊙ | X | Δ | Δ | X |
| | Adhesion property | PET (easy adhesion) | 100/100 | 100/100 | 100/100 | 100/100 | 100/100 | 100/100 | 100/100 | 100/100 | 100/100 | 100/100 | 40/100 | 0/100 |
| | | PET (non-treated) | 90/100 | 80/100 | 100/100 | 60/100 | 100/100 | 100/100 | 70/100 | 70/100 | 0/100 | 20/100 | 0/100 | 0/100 |
| | | PC | 80/100 | 100/100 | 90/100 | 70/100 | 90/100 | 100/100 | 100/100 | 100/100 | 80/100 | 50/100 | 20/100 | 0/100 |
| | | Acryl plate | 100/100 | 80/100 | 100/100 | 90/100 | 100/100 | 100/100 | 90/100 | 60/100 | 0/100 | 00/100 | 0/100 | 0/100 |
| | Moisture resistance | | ○ | ⊙ | Δ | ⊙ | ⊙ | ○ | ⊙ | ○ | Δ | Δ | Δ | X |

TABLE 6

| | | | Evaluation Example | | | | | | | | Comparative Evaluation Example | | | |
|---|---|---|---|---|---|---|---|---|---|---|---|---|---|---|
| | | | D-1 | D-2 | D-3 | D-4 | D-5 | D-6 | D-7 | D-8 | D-10 | D-11 | D-12 | D-13 |
| Urethane oligomer | | UT-1 | 23 | | | | | | | | | | | |
| | | UT-2 | | 22 | | | | | | | | | | |
| | | UT-3 | | | 47 | | | | | | | | | |
| | | UT-4 | | | | 40 | | | | | | | | |
| | | UT-5 | | | | | | | | | | | | |
| | | UT-5 | | | | | 46 | | | | | | | |
| | | UT-6 | | | | | | 30 | | | | | | |
| | | UT-7 | | | | | | | 60 | | | | | |
| | | UT-8 | | | | | | | | 45 | | | | |
| | | UA-1 | | | | | | | | | 40 | | | |
| | | UA-2 | | | | | | | | | | 24 | | |
| | | UA-3 | | | | | | | | | | | 38 | |
| | | UA-4 | | | | | | | | | | | | 32 |
| | | UV-7600B | 16 | 30 | 12 | | | 20 | | | 10 | 25 | 20 | 30 |
| Polyfunctional acrylate | | PETA | 20 | 8 | | 10 | 10 | | | | 20 | | | |
| | | DPHA | 12 | | 13 | | 10 | 20 | 18 | | | 17 | 18 | |
| Other monomers | | "ACMO" | 17 | 5 | 20 | 20 | | 18 | 12 | | 12 | | 10 | 13 |
| | | "DMAA" | | 15 | | 10 | 22 | | | | 8 | 4 | | 20 |
| | | THFA | 12 | | | | 7 | | 10 | | | | 14 | |
| | | IBOA | | 20 | 8 | 20 | | 12 | | | 10 | 10 | | |

TABLE 6-continued

|  |  | Evaluation Example | | | | | | | | Comparative Evaluation Example | | | |
|---|---|---|---|---|---|---|---|---|---|---|---|---|---|
|  |  | D-1 | D-2 | D-3 | D-4 | D-5 | D-6 | D-7 | D-8 | D-10 | D-11 | D-12 | D-13 |
| Solvent | MEK |  |  |  |  |  |  | 10 |  |  |  |  |  |
| Photopolymerization initiator | Irgacure1173 | 3 | 3 | 3 | 3 | 3 | 3 | 3 | 3 | 3 | 3 | 3 | 3 |
| Characteristics of coating film | Compatibility | ⊙ | ⊙ | ⊙ | ⊙ | ⊙ | ⊙ | ⊙ | ⊙ | Δ | ⊙ | ⊙ | X |
|  | Wettability PET (easy adhesion) | ⊙ | ⊙ | ⊙ | ⊙ | ⊙ | ⊙ | ⊙ | ⊙ | ○ | ⊙ | Δ | Δ |
|  | PET (non-treated) | ⊙ | ⊙ | ⊙ | ⊙ | ⊙ | ⊙ | ⊙ | ○ | Δ | Δ | Δ | Δ |
|  | PC | ○ | ⊙ | ⊙ | ⊙ | ⊙ | ⊙ | ⊙ | ⊙ | ○ | ⊙ | Δ | Δ |
|  | PMMA | ⊙ | ⊙ | ⊙ | ⊙ | ⊙ | ○ | ○ | ○ | Δ | Δ | Δ | Δ |
|  | Curing property | ⊙ | ○ | ⊙ | ⊙ | ⊙ | ⊙ | ○ | ○ | ⊙ | Δ | ○ | ⊙ |
|  | Tack resistance | ○ | ○ | Δ | ○ | ⊙ | ⊙ | ○ | ○ | ○ | Δ | Δ | ⊙ |
|  | Shrinkage resistance | ⊙ | ⊙ | ⊙ | ⊙ | ⊙ | ⊙ | ⊙ | Δ | X | X | ○ | X |
|  | Scratch resistance | ○ | ○ | ○ | ○ | ⊙ | ⊙ | ⊙ | ⊙ | ⊙ | Δ | Δ | ⊙ |
|  | Self restoring property | ⊙ | ○ | ○ | ○ | ⊙ | ⊙ | ⊙ | ⊙ | X | Δ | Δ | X |
|  | Adhesion property PET (easy adhesion) | 100/100 | 100/100 | 100/100 | 100/100 | 100/100 | 100/100 | 100/100 | 100/100 | 100/100 | 100/100 | 40/100 | 0/100 |
|  | PET (non-treated) | 90/100 | 80/100 | 100/100 | 60/100 | 100/100 | 100/100 | 70/100 | 70/100 | 0/100 | 20/100 | 0/100 | 0/100 |
|  | PC | 80/100 | 100/100 | 90/100 | 70/100 | 90/100 | 100/100 | 100/100 | 100/100 | 80/100 | 50/100 | 20/100 | 0/100 |
|  | Acryl plate | 100/100 | 80/100 | 100/100 | 90/100 | 100/100 | 100/100 | 90/100 | 60/100 | 0/100 | 00/100 | 0/100 | 0/100 |
|  | Moisture resistance | ○ | ⊙ | Δ | ⊙ | ⊙ | ○ | ⊙ | ○ | Δ | Δ | Δ | X |

TABLE 7

|  |  | Evaluation Example | | | | | | | | Comparative Evaluation Example | | | |
|---|---|---|---|---|---|---|---|---|---|---|---|---|---|
|  |  | E-1 | E-2 | E-3 | E-4 | E-5 | E-6 | E-7 | E-8 | E-9 | E-10 | E-11 | E-12 |
| Urethane oligomer | UT-1 | 42 |  |  | 2 |  |  |  |  |  |  |  |  |
|  | UT-2 |  | 30 |  |  |  |  |  |  |  |  |  |  |
|  | UT-3 |  | 8 | 35 |  |  |  |  |  |  |  |  |  |
|  | UT-4 |  |  |  | 38 |  |  |  |  |  |  |  |  |
|  | UT-5 |  |  |  |  |  |  |  |  |  |  |  |  |
|  | UT-5 |  |  |  |  | 50 |  |  |  |  |  |  |  |
|  | UT-6 |  |  |  |  |  | 40 |  |  |  |  |  |  |
|  | UT-7 |  |  |  |  |  |  | 45 |  |  |  |  |  |
|  | UT-8 |  |  |  |  |  |  |  | 35 |  |  |  |  |
|  | UA-1 |  |  |  |  |  |  |  |  | 50 |  |  |  |
|  | UA-2 |  |  |  |  |  |  |  |  |  | 36 |  |  |
|  | UA-3 |  |  |  |  |  |  |  |  |  |  | 40 |  |
|  | UA-4 |  |  |  |  |  |  |  |  |  |  |  | 50 |
| Monomer | "ACMO" |  |  |  |  | 20 | 20 |  |  | 20 | 20 | 14 |  |
|  | "HEAA" | 20 |  | 17 | 20 | 10 | 15 | 10 |  |  |  | 20 | 20 |
|  | "DEAA" | 10 | 12 |  |  |  | 20 | 18 | 10 |  | 20 |  | 5 |
|  | 4HBA | 15 | 20 | 10 | 10 |  |  | 12 |  |  | 10 | 10 |  |
|  | A-LEN-10 | 13 | 12 | 25 | 10 |  | 13 |  | 15 |  | 20 | 20 | 25 |
|  | IBOA |  | 18 | 13 |  | 20 | 12 | 15 | 20 | 30 |  | 10 |  |
| Photopolymerization initiator | DarocurTPO | 2 | 2 | 2 | 2 | 2 | 2 | 2 | 2 | 2 | 2 | 2 | 2 |
|  | Irgacure184 | 2 | 2 | 2 | 2 | 2 | 2 | 2 | 2 | 2 | 2 | 2 | 2 |
| Characteristics of sealing agent | Transmittance (%) | ⊙ | ⊙ | ⊙ | ⊙ | ⊙ | ⊙ | ⊙ | ⊙ | X | ⊙ | ⊙ | X |
|  | Light resistance | ○ | ○ | ○ | ○ | ⊙ | ○ | ⊙ | ⊙ | Δ | ⊙ | ⊙ | Δ |
|  | Water resistance | ○ | ○ | Δ | Δ | ○ | ○ | ○ | ⊙ | Δ | X | Δ | X |
|  | Evaluation of out gas generation | ⊙ | ⊙ | ⊙ | ⊙ | ⊙ | ⊙ | ⊙ | ⊙ | X | X | Δ | X |
|  | Heat cycle resistance | ○ | ○ | ○ | ○ | ⊙ | ⊙ | ⊙ | ⊙ | ⊙ | ⊙ | Δ | ⊙ |

TABLE 8

|  |  | Evaluation Example | | | | | | | | | Comparative Evaluation Example | | | |
|---|---|---|---|---|---|---|---|---|---|---|---|---|---|---|
|  |  | F-1 | F-2 | F-3 | F-4 | F-5 | F-6 | F-7 | F-8 | F-9 | F-10 | F-11 | F-12 | F-13 |
| Urethane oligomer | UT-1 | 9 | 17 |  |  |  |  |  |  |  |  |  |  |  |
|  | UT-2 |  |  | 12 |  |  |  |  |  |  |  |  |  |  |
|  | UT-3 |  |  |  | 14 |  |  |  |  |  |  |  |  |  |

TABLE 8-continued

|  |  | Evaluation Example | | | | | | | | | Comparative Evaluation Example | | | |
|---|---|---|---|---|---|---|---|---|---|---|---|---|---|---|
|  |  | F-1 | F-2 | F-3 | F-4 | F-5 | F-6 | F-7 | F-8 | F-9 | F-10 | F-11 | F-12 | F-13 |
|  | UT-4 |  |  |  |  | 10 |  |  |  |  |  |  |  |  |
|  | UT-5 |  |  |  |  |  |  |  |  |  |  |  |  |  |
|  | UT-5 |  |  |  |  |  | 10 |  |  |  |  |  |  |  |
|  | UT-6 |  |  |  |  |  |  | 8 |  |  |  |  |  |  |
|  | UT-7 |  |  |  |  |  |  |  | 10 |  |  |  |  |  |
|  | UT-8 |  |  |  |  |  |  |  |  | 15 |  |  |  |  |
|  | UA-1 |  |  |  |  |  |  |  |  |  | 13 |  |  |  |
|  | UA-2 |  |  |  |  |  |  |  |  |  |  | 10 |  |  |
|  | UA-3 |  |  |  |  |  |  |  |  |  |  |  | 5 |  |
|  | UA-4 |  |  |  |  |  |  |  |  |  |  |  |  | 5 |
| Polyfunctional acrylate | HDDA | 35 | 15 |  | 10 | 20 | 24 | 21 | 15 | 13 | 11 |  | 27 |  |
|  | TPGDA |  | 12 | 27 | 20 |  | 12 |  | 20 | 22 | 20 | 30 | 11 | 20 |
| Other monomers | "DEAA" |  | 22 | 20 | 16 | 30 | 30 | 15 | 19 |  | 20 | 46 | 24 | 9 |
|  | THFA | 30 | 28 | 10 | 34 | 34 | 18 | 20 | 30 | 17 |  |  | 27 | 20 |
|  | IBOA | 20 |  | 25 |  |  |  | 30 |  | 27 | 30 | 8 |  | 40 |
| Pigment |  | 3 | 3 | 3 | 3 | 3 | 3 | 3 | 3 | 3 | 3 | 3 | 3 | 3 |
| Pigment dispersant |  | 3 | 3 | 3 | 3 | 3 | 3 | 3 | 3 | 3 | 3 | 3 | 3 | 3 |
| Photopolymerization initiator | IrgacureTPO | 5 | 5 | 5 | 5 | 5 | 5 | 5 | 5 | 5 | 5 | 5 | 5 | 5 |
| Characteristics of printed matter | Viscosity [mPa·s] | 10 | 18 | 18 | 17 | 16 | 15 | 17 | 14 | 14 | 24 | 13 | 30 | 20 |
|  | Compatibility | ⊙ | ⊙ | ⊙ | ⊙ | ⊙ | ⊙ | ⊙ | ⊙ | ⊙ | Δ | Δ | ⊙ | X |
|  | Curing property | ⊙ | ○ | ⊙ | ○ | ⊙ | ⊙ | ⊙ | ⊙ | ⊙ | ⊙ | Δ | Δ | ⊙ |
|  | Surface dryness | ⊙ | ○ | ⊙ | ○ | ⊙ | ⊙ | ⊙ | ⊙ | ⊙ | ⊙ | Δ | Δ | ○ |
|  | Discharge stability | ⊙ | ○ | ⊙ | ○ | ⊙ | ○ | ⊙ | ⊙ | ○ | ○ | X | X | Δ |
|  | Sharpness | ○ | ⊙ | ○ | ⊙ | ○ | ⊙ | ⊙ | ⊙ | ⊙ | X | ○ | ○ | X |
|  | Water resistance | ⊙ | ⊙ | ○ | ○ | ○ | ⊙ | ⊙ | ○ | ⊙ | Δ | Δ | ○ | X |

TABLE 9

|  |  | Evaluation Example | | | | | | | | Comparative Evaluation Example | | | |
|---|---|---|---|---|---|---|---|---|---|---|---|---|---|
|  |  | G-1 | G-2 | G-3 | G4 | G-5 | G-6 | G-7 | G-8 | G-9 | G-10 | G-11 | G-12 |
| Urethane oligomer | UT-1 | 25 |  |  |  |  |  |  |  |  |  |  |  |
|  | UT-2 |  | 20 |  |  |  |  |  |  |  |  |  |  |
|  | UT-3 |  |  | 20 |  |  |  |  |  |  |  |  |  |
|  | UT-4 |  |  |  | 10 |  |  |  |  |  |  |  |  |
|  | UT-5 |  |  |  |  | 15 |  |  |  |  |  |  |  |
|  | UT-6 |  |  |  |  |  | 10 |  |  |  |  |  |  |
|  | UT-7 |  |  |  |  |  |  | 25 |  |  |  |  |  |
|  | UT-8 |  |  |  |  |  |  |  | 15 |  |  |  |  |
|  | UA-1 |  |  |  |  |  |  |  |  | 42 |  |  |  |
|  | UA-2 |  |  |  |  |  |  |  |  |  | 20 |  |  |
|  | UA-3 |  |  |  |  |  |  |  |  |  |  | 30 |  |
|  | UA-4 |  |  |  |  |  |  |  |  |  |  |  | 20 |
| Acrylamide containing hydroxyl group | HEAA | 30 | 10 | 50 | 40 | 33 | 55 | 30 | 20 | 30 | 20 | 27 | 27 |
|  | HEMAA | 10 | 18 | 19 |  |  |  | 10 | 20 |  |  | 10 | 20 |
| Diluent | UNIOL D400 | 10 | 10 |  | 27 | 20 |  | 10 |  |  | 57 |  |  |
|  | Ethylene glycol |  |  |  |  |  | 12 |  | 30 |  |  | 20 |  |
|  | PEG200 |  |  | 29 |  |  |  |  |  |  |  |  |  |
|  | UNIOL D1000 | 22 |  |  |  |  |  | 22 |  | 25 |  |  | 30 |
|  | Propylene glycol |  |  |  | 8 |  | 20 |  |  |  |  |  |  |
| Reactive diluent | 4HBA |  | 10 |  |  | 10 |  |  | 12 |  |  | 10 |  |
|  | IBOA |  |  |  | 20 |  | 20 |  |  |  |  |  |  |
| Photopolymerization initiator | Irgacure184 | 3 | 3 | 3 | 3 | 3 | 3 | 3 | 3 | 3 | 3 | 3 | 3 |
| Characteristics of resin composition | Curing property | ○ | ⊙ | ⊙ | ⊙ | ⊙ | ⊙ | ⊙ | ⊙ | ⊙ | Δ | X | ⊙ |
|  | PET-PET adhesive force | ⊙ | ⊙ | ⊙ | ⊙ | ⊙ | ⊙ | ⊙ | ⊙ | X | ○ | ○ | X |
|  | Adhesion property PET (easy adhesion) | 100/100 | 100/100 | 100/100 | 95/100 | 90/100 | 100/100 | 100/100 | 100/100 | 0/100 | 100/100 | 20/100 | 0/100 |
|  | PMMA | 100/100 | 100/100 | 90/100 | 95/100 | 80/100 | 90/100 | 100/100 | 100/100 | 0/100 | 30/100 | 0/100 | 0/100 |
|  | Hardness Shore A | 20 | 10 | 5 | 10 | 16 | 10 | 20 | 30 | 60 | 3 | 20 | 25 |
|  | Bleed out resistance | ⊙ | ○ | ⊙ | ⊙ | ⊙ | ⊙ | ⊙ | ⊙ | ⊙ | X | X | ⊙ |

TABLE 10

| | | Evaluation Example | | | | | | | | Comparative Evaluation Example | | | |
|---|---|---|---|---|---|---|---|---|---|---|---|---|---|
| | | H-1 | H-2 | H-3 | H-4 | H-5 | H-6 | H-7 | H-8 | H-9 | H-10 | H-11 | H-12 |
| Urethane oligomer | UT-1 | 40 | | | | | | | | | | | |
| | UT-2 | | 32 | | | | | | | | | | |
| | UT-3 | | | 20 | | | | | | | | | |
| | UT-4 | | | | 23 | | | | | | | | |
| | UT-5 | | | | | | | | | | | | |
| | UT-5 | | | | | 30 | | | | | | | |
| | UT-6 | | | | | | 23 | | | | | | |
| | UT-7 | | | | | | | 20 | | | | | |
| | UT-8 | | | | | | | | 30 | | | | |
| | UA-1 | | | | | | | | | 28 | | | |
| | UA-2 | | | | | | | | | | 38 | | |
| | UA-3 | | | | | | | | | | | 40 | |
| | UA-4 | | | | | | | | | | | | 35 |
| | UV-3700B | 12 | | 10 | 17 | | 17 | | 20 | 22 | | 27 | 20 |
| | UA-4200 | | 18 | | | 10 | | 20 | | | 22 | | |
| Other monomers | "HEAA" | | 15 | 20 | 20 | | 10 | 12 | | 10 | | | 10 |
| | "ACMO" | 20 | | 13 | | 25 | 28 | 18 | 15 | 25 | 15 | 13 | 35 |
| | IBMA | 18 | 10 | 22 | 20 | 15 | 12 | 11 | 25 | | | | |
| | CHMA | 10 | 25 | 15 | 20 | 20 | 10 | 19 | 10 | 15 | 25 | 20 | |
| Photopolymerization initiator | Irgacure1173 | 3 | 3 | 3 | 3 | 3 | 3 | 3 | 3 | 3 | 3 | 3 | 3 |
| Characteristics of coating film | Curing property | ⊙ | ○ | ⊙ | ⊙ | ○ | ⊙ | ○ | ⊙ | ⊙ | Δ | Δ | ○ |
| | Smoothness | ○ | ○ | ○ | ○ | ⊙ | ○ | ⊙ | ⊙ | ⊙ | Δ | X | X |
| | Glossiness | ○ | ○ | ○ | ○ | ⊙ | ○ | ⊙ | ⊙ | Δ | Δ | X | Δ |
| | Adhesion property | ⊙ | ⊙ | ⊙ | ○ | ⊙ | ⊙ | ⊙ | ⊙ | Δ | X | X | ○ | X |
| | Removability | ⊙ | ○ | ⊙ | ○ | ⊙ | ○ | ⊙ | ○ | ○ | ○ | ○ | ○ |

TABLE 11

| | | Evaluation Example | | | | | | | | Comparative Evaluation Example | | | |
|---|---|---|---|---|---|---|---|---|---|---|---|---|---|
| | | I-1 | I-2 | I-3 | I-4 | I-5 | I-6 | I-7 | I-8 | I-9 | I-10 | I-11 | I-12 |
| Urethane oligomer | UT-1 | 25 | | | | | | | | | | | |
| | UT-2 | | 20 | | | | | | | | | | |
| | UT-3 | | | 35 | | | | | | | | | |
| | UT-4 | | | | 30 | | | | | | | | |
| | UT-5 | | | | | 20 | | | | | | | |
| | UT-6 | | | | | | 30 | | | | | | |
| | UT-7 | | | | | | | 35 | | | | | |
| | UT-8 | | | | | | | | 40 | | | | |
| | UA-1 | | | | | | | | | 32 | | | |
| | UA-2 | | | | | | | | | | 38 | | |
| | UA-3 | | | | | | | | | | | 40 | |
| | UA-4 | | | | | | | | | | | | 35 |
| Monomer | Light acrylate PE-4A | 45 | 40 | 35 | 30 | 40 | 40 | 40 | 40 | 28 | 32 | 30 | 35 |
| | ACMO | 10 | 10 | 10 | 10 | | 20 | 10 | | 20 | | | |
| | DPHA | 20 | 20 | 20 | 15 | 20 | 10 | 10 | 20 | | 10 | 18 | 18 |
| | TMPTA | 10 | 10 | | 15 | 20 | | 5 | | 20 | 20 | 12 | 12 |
| Photopolymerization initiator | Irgacure1173 | 3 | 3 | 3 | 3 | 3 | 3 | 3 | 3 | 3 | 3 | 3 | 3 |
| Surface modifying agent | 8019add | 0.5 | 0.5 | 0.5 | 0.5 | 0.5 | 0.5 | 0.5 | 0.5 | 0.5 | 0.5 | 0.5 | 0.5 |
| Characteristics of protecting agent | Transparency | ⊙ | ⊙ | ⊙ | ⊙ | ⊙ | ⊙ | ⊙ | ⊙ | X | ⊙ | ⊙ | X |
| | Weather resistance | ○ | ○ | ○ | ○ | ⊙ | ○ | ⊙ | ○ | Δ | ○ | ⊙ | Δ |
| | Water resistance | ○ | ○ | Δ | ○ | ⊙ | ○ | ○ | ○ | Δ | X | ○ | X |
| | Adhesion property | ⊙ | ⊙ | ⊙ | ⊙ | ⊙ | ⊙ | ⊙ | ⊙ | Δ | X | X | Δ |
| | Abrasion resistance | ○ | ○ | ○ | ⊙ | ⊙ | ⊙ | ⊙ | ⊙ | ⊙ | ⊙ | X | X |
| | Scratch resistance | ○ | ○ | Δ | ⊙ | ⊙ | ⊙ | ⊙ | ⊙ | ⊙ | ⊙ | X | Δ |

TABLE 12

|  |  | Evaluation Example | | | | | | | | Comparative Evaluation Example | | | |
|---|---|---|---|---|---|---|---|---|---|---|---|---|---|
|  |  | J-1 | J-2 | J-3 | J-4 | J-5 | J-6 | J-7 | J-8 | J-9 | J-10 | J-11 | J-12 |
| Urethane oligomer | UT-1 | 60 |  | 5 |  |  |  |  |  |  |  |  |  |
|  | UT-2 | 5 | 65 |  | 2 |  |  |  |  | 8 |  | 10 |  |
|  | UT-3 |  |  | 55 |  |  |  |  |  |  |  |  |  |
|  | UT-4 |  |  |  | 68 | 10 | 12 |  |  |  | 5 |  |  |
|  | UT-5 |  |  |  |  | 60 |  |  |  |  |  |  |  |
|  | UT-6 |  |  |  |  |  | 50 |  |  |  |  |  |  |
|  | UT-7 |  |  |  |  |  |  | 66 |  |  |  |  |  |
|  | UT-8 |  |  |  |  |  |  |  | 70 |  |  |  |  |
|  | UA-1 |  |  |  |  |  |  |  |  | 62 |  |  |  |
|  | UA-2 |  |  |  |  |  |  |  |  |  | 65 |  |  |
|  | UA-3 |  |  |  |  |  |  |  |  |  |  | 60 |  |
|  | UA-4 |  |  |  |  |  |  |  |  |  |  |  | 70 |
| Polyfunctional | HDDA | 11 | 5 | 10 | 5 | 5 | 10 | 4 | 10 |  | 10 | 20 | 10 |
| acrylate | DPHA | 20 | 20 | 25 | 15 | 20 | 18 | 20 | 10 | 20 | 15 |  | 12 |
| Other monomers | "ACMO" |  | 7 | 5 | 5 | 4 | 10 | 5 |  | 10 |  | 4 | 2 |
|  | IBOA | 4 | 3 |  | 5 | 1 |  | 5 | 10 |  | 5 | 6 | 6 |
| Silica microparticles | IPA-ST-L | 10 | 10 | 10 | 10 | 10 | 10 | 10 | 10 | 10 | 10 | 10 | 10 |
| Solvent | MEK | 50 | 50 | 50 | 50 | 50 | 50 | 50 | 50 | 50 | 50 | 50 | 50 |
| Photopolymerization initiator | Irgacure184 | 3 | 3 | 3 | 3 | 3 | 3 | 3 | 3 | 3 | 3 | 3 | 3 |
| Characteristics of decorative film | Transmittance | ⊙ | ⊙ | ⊙ | ⊙ | ⊙ | ⊙ | ⊙ | ⊙ | Δ | ⊙ | ⊙ | Δ |
|  | Blocking resistance | ○ | Δ | ○ | ○ | ○ | ○ | ⊙ | ⊙ | ⊙ | X | X | ○ |
|  | Elongation at break | ⊙ | ○ | ⊙ | ○ | ○ | ○ | ○ | ○ | ○ | ⊙ | ⊙ | X |
|  | Molding processability | ⊙ | ○ | ○ | ⊙ | ○ | ○ | ○ | ○ | X | ○ | Δ | X |
|  | Curing property | ⊙ | ○ | ⊙ | ⊙ | ⊙ | ⊙ | ⊙ | ⊙ | ⊙ | Δ | ○ | Δ |
| Adhesion property | PET (easy adhesion) | 100/100 | 100/100 | 100/100 | 100/100 | 100/100 | 100/100 | 100/100 | 100/100 | 100/100 | 70/100 | 50/100 | 50/100 |
|  | PC | 100/100 | 100/100 | 100/100 | 100/100 | 80/100 | 100/100 | 100/100 | 100/100 | 30/100 | 70/100 | 0/100 | 0/100 |
|  | ABS | 100/100 | 100/100 | 100/100 | 100/100 | 80/100 | 100/100 | 100/100 | 100/100 | 30/100 | 0/100 | 0/100 | 0/100 |
|  | Pencil hardness | ○ | ○ | ○ | ○ | ⊙ | ⊙ | ○ | ⊙ | ⊙ | ○ | Δ | Δ |
|  | Scratch resistance | ○ | ○ | ○ | ○ | ⊙ | ⊙ | ○ | ⊙ | ⊙ | ○ | Δ | X |
|  | Bending resistance | ⊙ | ⊙ | ⊙ | ○ | ⊙ | ⊙ | ⊙ | ○ | X | X | ⊙ | Δ |

INDUSTRIAL APPLICABILITY

As explained in the above, the (meth)acrylamide based urethane oligomer of the present invention is a (meth)acrylamide based urethane oligomer which has at least one (meth)acrylamide group at the end or in the side chain, and 5% by weight or less of content of a low molecular weight component like urethane adduct. Due to such reasons, it exhibits excellent compatibility with general purpose organic solvents and monomers, exhibits a high curing property according to active energy ray irradiation, and has favorable surface dryness of a cured film. As the active energy ray cure shrinkage rate of the (meth)acrylamide based urethane oligomer of the present invention is not greater than 5%, it has excellent curing resistant shrinkage rate. Accordingly, a cured film having an adhesion property, shrinkage resistance, and high moisture and heat resistance can be produced. Furthermore, if necessary, by using it after mixing with a monofunctional or polyfunctional monomer, an ionic monomer, an active energy ray polymerization initiator, a pigment, or the like, it can be suitably used for applications like cohesive adhesive agents, electronic materials, ink, coating agents, and resists of photocuring type.

The invention claimed is:

1. A (meth)acrylamide based urethane oligomer which has one or two or more kinds of a skeleton selected from an ether skeleton, an ester skeleton, a silicone skeleton, or an acryl skeleton in a molecule, at least one (meth)acrylamide group, and a shrinkage rate of 5.0% or less before and after active energy curing, said (meth)acrylamide based urethane oligomer having a number average molecular weight of 4,500 to 30,000, and acryl equivalents within a range of from 750 to 25,000.

2. The (meth)acrylamide based urethane oligomer according to claim 1, wherein content of a component having molecular weight of less than 1000 (excluding (meth)acrylamide having a hydroxyl group) is 5% by weight or less.

3. The (meth)acrylamide based urethane oligomer according to claim 1, wherein (meth)acrylamide (C) having a hydroxyl group is represented by formula [1]:

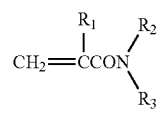

[1]

wherein, $R_1$ represents a hydrogen atom or a methyl group, $R_2$ and $R_3$ may be the same or different from each other, $R_2$ and $R_3$ may be a linear or branched alkyl group having 1 to 6 carbon atoms or an aliphatic ring or an aromatic ring having 3 to 6 carbon atoms, which may be substituted with a hydrogen atom or a hydroxyl group and, $R_2$ and $R_3$ may form, together with the nitrogen atom attached, a saturated or unsaturated 5- to 7-membered ring in which 5- to 7-membered ring, an oxygen atom or a nitrogen atom other than the aforementioned nitrogen atom may be additionally contained, with the proviso that $R_2$ and $R_3$ are not both a hydrogen atom and $R_2$ and $R_3$ are not both an alkyl group and that $R_2$ and $R_3$ have one or more hydroxyl groups in total wherein said (meth)acrylamide based urethane oligomer is produced by a reaction of a polyol (A) having at least one hydroxyl group in one molecule and one or more skeleton(s) selected from an ether skeleton, ester skeleton, silicone skeleton, or acryl skeleton, polyisocyanate (B) having at least two isocyanate groups in one molecule, and (meth)acrylamide (C).

4. An active energy ray curable resin composition comprising 1% by weight or more of the (meth)acrylamide based urethane oligomer according to claim 1.

5. An active energy ray curable cohesive composition comprising 1% by weight or more of the (meth)acrylamide based urethane oligomer according to claim 1.

6. An active energy ray curable adhesive composition comprising 1% by weight or more of the (meth)acrylamide based urethane oligomer according to claim 1.

7. An active energy ray curable coating agent composition comprising 1% by weight or more of the (meth)acrylamide based urethane oligomer according to claim 1.

8. An active energy ray curable sealing agent composition comprising 1% by weight or more of the (meth)acrylamide based urethane oligomer according to claim 1.

9. An active energy ray curable inkjet ink composition comprising 1% by weight or more of the (meth)acrylamide based urethane oligomer according to claim 1.

10. An active energy ray curable resin composition for three-dimensional object formation comprising 1% by weight or more of the (meth)acrylamide based urethane oligomer according to claim 1.

11. An active energy ray curable nail decorating agent composition comprising 1% by weight or more of the (meth)acrylamide based urethane oligomer according to claim 1.

12. An active energy ray curable car exterior protecting agent composition comprising 1% by weight or more of the (meth)acrylamide based urethane oligomer according to claim 1.

13. An active energy ray curable resin composition for decorative film comprising 1% by weight or more of the (meth)acrylamide based urethane oligomer according to claim 1.

* * * * *